(12) United States Patent
Okuda et al.

(10) Patent No.: US 8,145,267 B2
(45) Date of Patent: Mar. 27, 2012

(54) BIOLOGICAL SAMPLE MEASUREMENT APPARATUS

(75) Inventors: Eiji Okuda, Ehime (JP); Akiyoshi Oozawa, Ehime (JP); Kazuo Manabe, Ehime (JP)

(73) Assignee: Panasonic Corporation, Osaka (JP)

( * ) Notice: Subject to any disclaimer, the term of this patent is extended or adjusted under 35 U.S.C. 154(b) by 231 days.

(21) Appl. No.: 12/664,768

(22) PCT Filed: Dec. 29, 2008

(86) PCT No.: PCT/JP2008/004045
§ 371 (c)(1),
(2), (4) Date: Dec. 15, 2009

(87) PCT Pub. No.: WO2009/087749
PCT Pub. Date: Jul. 16, 2009

(65) Prior Publication Data
US 2010/0190441 A1    Jul. 29, 2010

(30) Foreign Application Priority Data

Jan. 10, 2008 (JP) .................. 2008-003707
Jan. 11, 2008 (JP) .................. 2008-004717

(51) Int. Cl.
*H04M 1/00* (2006.01)
(52) U.S. Cl. ............ 455/556.1; 455/452.1; 455/452.2; 455/507; 455/509; 455/513; 455/514; 455/41.2; 455/154.1; 455/158.1; 600/300; 600/301
(58) Field of Classification Search .............. 455/556.1, 455/556.2, 557, 68–70, 522, 67.11, 67.15, 455/62, 41.2, 507–514, 452.1–452.2, 154.1, 455/158.1–158.3, 161.1–161.3; 600/300, 600/301
See application file for complete search history.

(56) References Cited

U.S. PATENT DOCUMENTS

| 6,223,043 | B1 | 4/2001 | Hazama |
| 2003/0013480 | A1 | 1/2003 | Endo |
| 2003/0129965 | A1* | 7/2003 | Siegel ............ 455/411 |
| 2004/0132490 | A1* | 7/2004 | Jerbi et al. ......... 455/556.1 |
| 2004/0166892 | A1* | 8/2004 | Iizuka ............ 455/550.1 |
| 2005/0226468 | A1* | 10/2005 | Deshpande et al. ..... 382/115 |

(Continued)

FOREIGN PATENT DOCUMENTS

EP          1 059 825        12/2000

(Continued)

OTHER PUBLICATIONS

International Search Report issued Feb. 10, 2009 in International (PCT) Application No. PCT/JP2008/004045.

(Continued)

*Primary Examiner* — Tuan A Tran
(74) *Attorney, Agent, or Firm* — Wenderoth, Lind & Ponack, L.L.P.

(57) ABSTRACT

A biological sample measurement apparatus includes a measurement component for detecting a blood glucose level, a transmitter for sending the detected blood glucose level to a portable terminal, a receiver for receiving an acknowledge signal and a portable terminal ID sent from the portable terminal, a storage component for associating the communication frequency at the point of successful communication with the received portable terminal ID and storing it as communication success history along with successful information from the past, and a communication frequency selector for selecting a communication frequency on the basis of this communication success history.

13 Claims, 15 Drawing Sheets

U.S. PATENT DOCUMENTS

2008/0045161 A1 * 2/2008 Lee et al. .................. 455/73

FOREIGN PATENT DOCUMENTS

| | | |
|---|---|---|
| JP | 8-163627 | 6/1996 |
| JP | 2001-359158 | 12/2001 |
| JP | 2002-251461 | 9/2002 |
| JP | 2003-32166 | 1/2003 |
| JP | 2003-61001 | 2/2003 |
| JP | 2003-208685 | 7/2003 |
| JP | 2006-208018 | 8/2006 |
| JP | 2006-270254 | 10/2006 |
| JP | 2007-60109 | 3/2007 |
| JP | 2007-189523 | 7/2007 |
| JP | 2007-198985 | 8/2007 |
| WO | 00/35233 | 6/2000 |
| WO | 02/078512 | 10/2002 |
| WO | 2007/105276 | 9/2007 |

OTHER PUBLICATIONS

Supplementary European Search Report issued Jul. 22, 2011 in European Application No. EP 08 86 9629.

* cited by examiner

| portable terminal ID | communication success frequency | | | | | | | | |
|---|---|---|---|---|---|---|---|---|---|
| | DATA0 | DATA1 | DATA2 | DATA3 | DATA4 | DATA5 | ... | DATA14 | DATA15 |
| | 2.44GHz | 2.42GHz | 2.43GHz | 2.47GHz | 2.46GHz | 2.41GHz | ... | 2.40GHz | 2.45GHz |
| | 2 | 1 | 2 | 1 | 3 | 2 | ... | 2 | 1 |

FIG. 6

| portable terminal ID | 1 | 2 | 3 |
|---|---|---|---|
| number of successful communications | 6 | 8 | 2 |
| communication success frequency | 2.42GHz | 2.44GHz | 2.46GHz |
| time series order | 2 | 1 | 3 |

FIG. 13

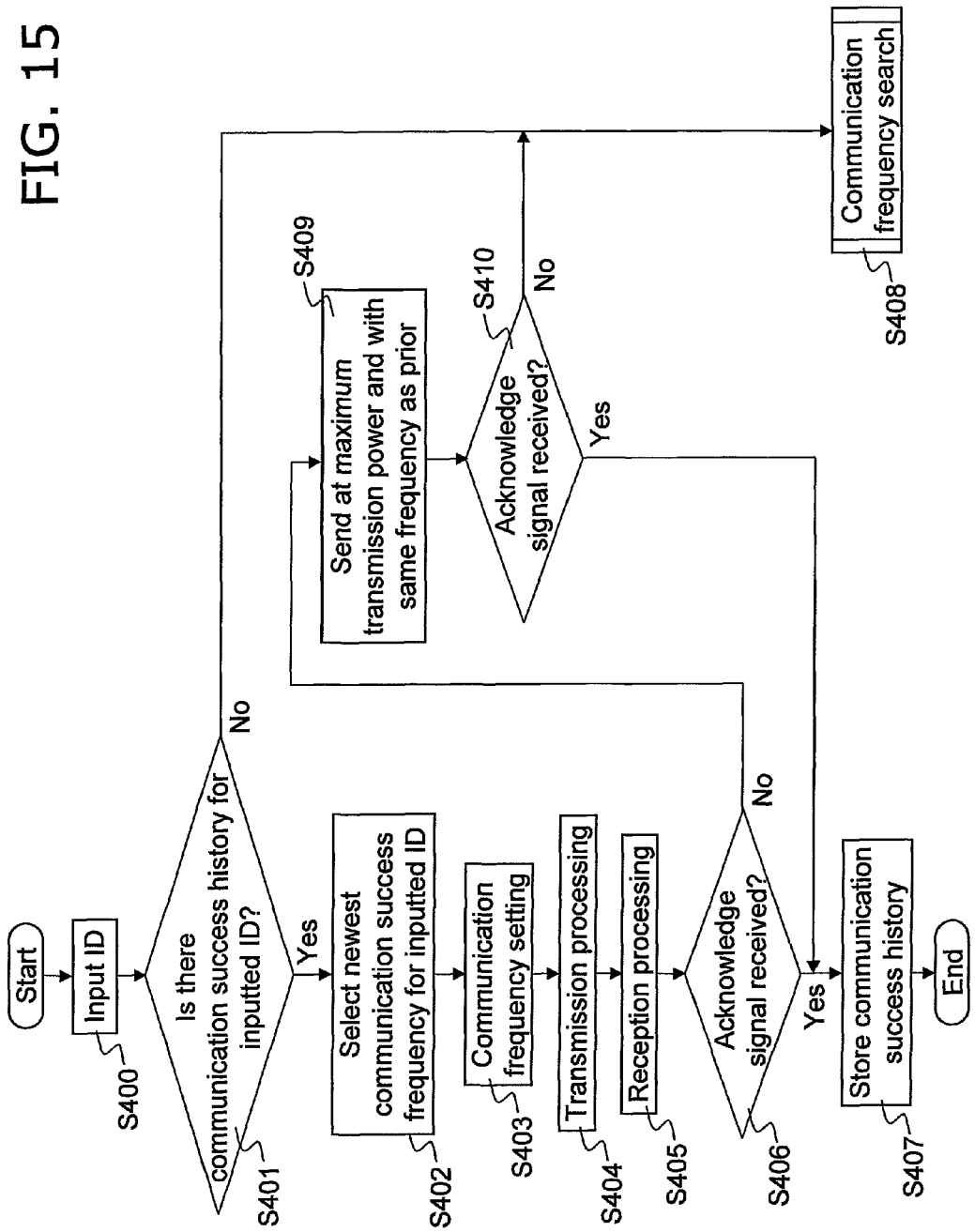

BIOLOGICAL SAMPLE MEASUREMENT APPARATUS

TECHNICAL FIELD

The present invention relates to a biological sample measurement apparatus that uses weak radio waves to perform short-range wireless communication with a portable terminal, and more particularly relates to a technique for determining a communication frequency at which communication between a biological sample measurement apparatus and a portable terminal is possible.

BACKGROUND ART

A blood glucose level measurement apparatus for measuring blood glucose levels is an example of a biological sample measurement apparatus that measures biological data. A wireless communication apparatus has been disclosed that is composed of this blood glucose level measurement apparatus and a portable terminal for acquiring the measured blood glucose level data by wireless communication (see Patent Citation 1, for example).

In the field of this kind of wireless communication apparatus, a technique has been disclosed in which a portable terminal performs reception intermittently in order to reduce power consumption during communication (see Patent Citation 2, for example).

Here, every time the blood glucose level measurement apparatus measures blood glucose levels, the blood glucose level measurement apparatus establishes communication with a portable terminal, and sends the blood glucose level data to this portable terminal.

Patent Citation 1: Japanese Laid-Open Patent Application 2002-251461
Patent Citation 2: Japanese Laid-Open Patent Application 2003-208685

DISCLOSURE OF INVENTION

Technical Problem

However, a blood glucose level measurement apparatus and a portable terminal usually each have their own individual frequency at which communication is possible. With prior art, even if communication is established with a specific portable terminal, or with one of various specific portable terminals, first a reference frequency has to be used to attempt to establish communication every time. Therefore, this creates problems in that it takes time every time communication is established, and other electronic devices are affected by unnecessary radio waves emitted during this period.

In view of this, it is an object of the present invention to provide a biological sample measurement apparatus with which a frequency at which communication is possible can be efficiently detected in communication between a biological sample measurement apparatus and a portable terminal.

Technical Solution

The biological sample measurement apparatus pertaining to the first invention is a biological sample measurement apparatus equipped with a function for wireless communication with a portable terminal, comprising a biological data measurement component, a transmitter, a receiver, a storage component, and a communication frequency selector. The biological data measurement component measures biological data. The transmitter sends the biological data measured by the biological data measurement component to the portable terminal. The receiver receives a portable terminal individual identification number emitted by the portable terminal and a communication success signal that is sent back from the portable terminal when the signal sent to the portable terminal is acknowledged by the portable terminal. The storage component associates the portable terminal individual identification number and a specific communication frequency when the communication success signal has been received, and stores these as communication success history. The communication frequency selector selects the specific communication frequency, and a communication frequency recorded in the communication success history is preferentially selected as the specific communication frequency.

Here, the communication frequency used by the transmitter and the portable terminal individual identification number received by the receiver are stored as communication success history in the storage component, the communication frequency selector selects the frequency on the basis of what is stored, and this frequency is used as the communication frequency by the transmitter in attempting communication.

The biological sample here is a blood glucose level, for example. Therefore, the biological sample measurement apparatus may be a blood glucose level measurement apparatus. The portable terminal individual identification number is an individual identification number (ID) that is unique to an individual portable terminal. The communication success signal is a signal indicating that communication has been carried out properly, and is generally called an acknowledge signal. Specifically, if an acknowledge signal is received, this means that communication has been established and data communication has been properly carried out. The storage component may store not only communication success history, but also history related to both successful and failed communication. Also, the communication success history is preferably stored as information combining the communication frequency when communication is successful and the portable terminal individual identification number of the portable terminal. This information may be stored in time series order every time communication is successful.

The method for ensuring successful communication with a conventional wireless communication system is to shift the communication frequency by predetermined intervals from a predetermined reference frequency, and search for the frequency at which communication is possible every time an attempt is made to establish communication.

However, even though generally a specific biological sample measurement apparatus communicates with a specific portable terminal, with the above-mentioned conventional structure, even when establishing communication with a specific portable terminal, or with one of various specific portable terminals, first a reference frequency has to be used to attempt to establish communication every time. Also, there are individual differences in the communication frequencies of portable terminals, and furthermore, even with a given portable terminal, the communication frequency will vary due to mechanical and environmental factors. Therefore, if the frequency at which communication is possible should diverge greatly from the specific reference frequency, for example, this creates problems in that it takes time every time communication is established, and other electronic devices are affected by unnecessary radio waves emitted during this period.

In view of this, the biological sample measurement apparatus of the present invention has a means for storing a communication frequency and a portable terminal individual identification number as communication success history when communication is successful in the past. Communication is attempted on the basis of this communication success history.

With a constitution such as this, for example, it is possible to use the most recent communication frequency with which communication is successful as the communication frequency used first to establish communication, or to preferentially use the communication frequency associated with a specific portable terminal individual identification number.

In light of the above facts that there are individual differences in communication frequency and communication is generally with a specific portable terminal, an attempt at communication using a communication frequency stored in communication success history, or an attempt at communication using a communication frequency associated with a specific portable terminal individual identification number, will make it possible for communication to be established more efficiently. Specifically, it is possible to attempt the establishment of communication by preferentially selecting a communication frequency with a higher probability of successful communication.

Therefore, it is possible to shorten the average time it takes until successful communication, or to reduce the emission of unnecessary radio waves.

The biological sample measurement apparatus pertaining to the second invention is the biological sample measurement apparatus pertaining to the first invention, wherein the communication frequency selector selects the communication frequency from among the communication success history in time series order, going backward from the most recent communication frequency.

Here, the communication frequency selector first selects as the communication frequency the most recent (latest) communication frequency in time series order from the communication success history, after which it selects the communication frequency in time series order, going backward in time.

With this constitution, since a portable terminal and a biological sample measurement apparatus are generally used as a paired system by the same user, and the combination is not frequently changed, it is possible to attempt to establish communication using at first the communication frequency that generally has the highest probability of successful communication at the start of communication.

Therefore, the likelihood of successful communication on the first attempt at establishing communication is higher, so it is possible to shorten the average time it takes until communication is successful.

The biological sample measurement apparatus pertaining to the third invention is the biological sample measurement apparatus pertaining to the first or second invention, wherein the communication frequency selector selects the communication frequency which has been stored so as to be associated with the portable terminal individual identification number that is the same as the portable terminal individual identification number associated with the communication frequency selected at the previous time by the communication frequency selector.

Here, the communication frequency selector successively selects from among the communication success history the communication frequency associated with the portable terminal individual identification number that is the same as the portable terminal individual identification number of the communication frequency selected immediately prior.

With this constitution, for example, the communication frequency selector selects the most recent communication frequency in time series order from the communication success history, and if the establishment of communication with this selected communication frequency is not successful, it selects the next communication frequency from the communication success history, and in this selection, it is possible to preferentially select the communication frequency stored with an associated portable terminal individual identification number that is the same as the portable terminal individual identification number stored and associated with the most recent communication frequency. Specifically, it is possible to attempt to establish communication by preferentially using only the communication frequency stored and associated with the same portable terminal individual identification number.

Also, even in communication with a given portable terminal, the frequency at which communication with that portable terminal is possible will vary with mechanical and environmental changes, for example. That is, it is highly probable that the same portable terminal is being used, but it is possible that the frequency at which communication is possible will vary.

Therefore, even if communication is not successful with the most recent communication frequency stored in the communication success history, with a biological sample measurement apparatus that generally involves the use of the same portable terminal, the average time it takes until successful communication can be shortened by performing communication preferentially on the basis of the history of communication that is successful in the past with the same portable terminal.

The biological sample measurement apparatus pertaining to the fourth invention is the biological sample measurement apparatus pertaining to any of the first to third inventions, wherein the communication frequency selector selects the communication frequency from among the most recent communication frequencies for the communication frequencies stored in association with each portable terminal individual identification number.

Here, the communication frequency selector selects the communication frequency from among the most recent communication frequencies for the various portable terminal individual identification numbers stored in the communication success history.

With this constitution, when the biological sample measurement apparatus is used by a plurality of users, for example, that is, when a single biological sample measurement apparatus communicates with any of various specific portable terminals, it is possible to efficiently select the most recent communication frequency from among the communication frequencies associated with a portable terminal individual identification number that is the same as that of the portable terminal being used.

Therefore, it is possible to establish communication efficiently even when using many specific portable terminals for a single biological sample measurement apparatus.

The biological sample measurement apparatus pertaining to the fifth invention is the biological sample measurement apparatus pertaining to any of the first to fourth inventions, wherein the communication frequency selector selects the communication frequency in descending order of the storage count for each portable terminal individual identification number in the communication success history.

Here, the communication frequency selector selects the communication frequency from among communication frequencies associated with a portable terminal individual identification numbers having more numerous successful communications, and until communication is successful, successively selects the communication frequencies stored in association with each portable terminal individual identification number, starting from the portable terminal individual identification number with the greatest number of successful communications and moving toward the portable terminal individual identification number with the fewest.

With this constitution, the communication frequency selector is able to select a communication frequency for a portable terminal that the user of the biological sample measurement apparatus has used in the past, in the order of the greatest number of successful communications (usage frequency) for each individual portable terminal. For example, if the number of successful communications is in the decreasing order of a first portable terminal individual identification number, a second portable terminal individual identification number, and a third portable terminal individual identification number, first the most recent communication frequency is selected in time series order from among the communication frequencies associated with the first portable terminal individual identification number, and an attempt to establish communication is made. Then, if this attempt does not result in successful communication, the most recent communication frequency is selected in time series order from among the communication frequencies associated with the second portable terminal individual identification number. Similarly, if the communication is not successful, the most recent communication frequency is selected from among the communication frequencies associated with the third portable terminal individual identification number.

Therefore, there is a higher probability that communication will be successfully established for the portable terminals that are used most often, and as a result, the average time it takes until communication is successful can be shortened.

The biological sample measurement apparatus pertaining to the sixth invention is the biological sample measurement apparatus pertaining to the fifth invention, wherein, in the communication success history, if the descending is the same in number for different portable terminal individual identification numbers, the communication frequency selector selects the communication frequency from among the communication frequencies stored in association with the portable terminal individual identification number that is the same number as the storage count, in time series order starting with the newest.

Here, if the number of times different portable terminal individual identification numbers have been stored in the communication success history is the same, a new communication frequency is preferentially selected in time series order from among the communication frequencies stored in association with these portable terminal individual identification numbers.

With this constitution, if a communication frequency is selected on the basis of the number of successful communications for each portable terminal, then even if the number of successful communications is the same, it will be possible to select from among these the communication frequency with the highest probability of successful communication, and thus the average time it takes until communication is established is shortened.

The biological sample measurement apparatus pertaining to the seventh invention is the biological sample measurement apparatus pertaining to any of the first to sixth inventions, further comprising an individual identification number input component with which the desired portable terminal individual identification number can be inputted.

Here, there is further provided an individual identification number input component with which the portable terminal individual identification number of the terminal to be communicated with can be inputted.

With this constitution, when the user of the biological sample measurement apparatus inputs a portable terminal individual identification number to the individual identification number input component, the communication frequency selector can preferentially select the communication frequency stored in association with the inputted portable terminal individual identification number from among the communication success history. Also, it is possible, for example, to select just the communication frequencies stored in association with an inputted portable terminal individual identification number, in time series order starting with the newest input.

Therefore, if the portable terminal individual identification number of a portable terminal to be communicated with is already known, it is possible to attempt to establish communication by preferentially using a communication frequency that is successful in the past with the portable terminal to be communicated with. As discussed above, there are individual differences in the communication frequencies of portable terminals. Therefore, since a communication frequency stored in association with the portable terminal individual identification number of the portable terminal being used is selected, the probability of successful communication is higher. As a result, it is possible to shorten the average time it takes until communication is successful.

The biological sample measurement apparatus pertaining to the eighth invention is the biological sample measurement apparatus pertaining to any of the first to seventh inventions, wherein if the receiver cannot receive the communication success signal even though the specific communication frequency is selected on the basis of the communication success history, the communication frequency selector repeatedly selects the communication frequency, focusing on a specific reference frequency and in increasing order of deviation from the specific reference frequency, until the receiver receives the communication success signal or until the deviation reaches or exceeds a specific value.

Here, if communication is not successful even when an attempt is made to establish communication using a communication frequency selected on the basis of the communication success history, first an attempt to establish communication is made using a reference frequency (such as 2.45 GHz) stored ahead of time in the storage component. If no communication success signal is received as a result of this attempt, communication frequencies are selected in increasing order of deviation from the reference frequency, and an attempt to establish communication is made every time. If in the course of this communication success signal is received, or if the selected communication frequency exceeds a specific frequency range, the attempt to establish communication is halted. If a communication success signal is received in the course of this, that communication frequency is termed the first optimal frequency.

With this constitution, even if communication is not successful when an attempt to establish communication is made on the basis of communication success history, it will be possible to search for a communication frequency that will afford successful communication.

Therefore, even if a portable terminal that has communicated one or more times should have its communication frequency changed due to a difference in environment or the like, so that communication is not successful even on the basis of communication success history, it will still be possible to increase the probability of successful communication.

Also, when a new portable terminal is used, or when a biological sample measurement apparatus is used for the first time, or when there is no history in the communication success history, for example, it will still be possible to increase the probability of successful communication.

The biological sample measurement apparatus pertaining to the ninth invention is the biological sample measurement apparatus pertaining to the eighth invention, wherein the deviation is a value obtained by adding or subtracting by a specific frequency value at a time.

Here, the communication frequency selector selects a value (F±n×ΔF; n=0, 1, 2, ...) obtained by adding or subtracting by a specific frequency interval (ΔF) to or from a reference frequency stored ahead of time in the storage component. For example, an attempt is made to establish communication by using a frequency (such as 2.451 GHz or 2.449 GHz) that deviates by a specific value (such as 1 MHz) from the reference frequency. Subsequently, communication frequencies are selected that similarly have been obtained by adding a specific value, and this is repeated until a communication success signal is received or until the deviation between the reference frequency and the communication frequency reaches a specific value (such as 1 GHz).

With this constitution, the number of communication frequencies selected by the communication frequency selector can be limited ahead of time, so the time allotted to attempting to establish communication can be set to a specific length of time.

Therefore, the user can ascertain within a specific length of time whether or not communication with a portable terminal is possible.

The biological sample measurement apparatus pertaining to the tenth invention is the biological sample measurement apparatus pertaining to the eighth or ninth invention, wherein the communication frequency selector selects a frequency in increasing order of deviation from a communication frequency selected when the receiver has received the communication success signal, and searches for a receivable frequency band that is a range of communication frequencies over which the receiver can receive the communication success signal.

Here, if a communication success signal cannot be received despite using a frequency band that has been stored as history information, a more optimal frequency band can be searched for during transmission and reception. More specifically, the frequency band is controlled so that the above-mentioned first optimal frequency is used as a reference and the deviation alternately increases and decreases in stages. For instance, if we let ΔF be a frequency that is increased in stages, let the number of stages (number of iterations) n be 10, and let B be a test reference frequency, then the frequency band is changed as B, B+1×ΔF, B−1×ΔF, B+2×ΔF, B−2×ΔF, ..., B+10×ΔF, B−10×ΔF, and the system checks to see if there is a communication success signal. The system searches for a receivable frequency band, which is a range over which a communication success signal can be received.

In testing the receivable frequency band, the number of stages may be set to a specific value, or it may be terminated at the point when reception becomes impossible.

Consequently, by selecting a receivable frequency band (such as calculating the average frequency value in the receivable frequency band), it is possible to control to a more optimal frequency band as compared to the above-mentioned first optimal frequency.

The biological sample measurement apparatus pertaining to the eleventh invention is the biological sample measurement apparatus pertaining to any of the eighth to tenth inventions, wherein the storage component stores as the optimal frequency the central frequency of the frequency band in the receivable frequency band.

Here, the method for selecting the optimal frequency from among the frequencies that can be received is to calculate the center of the receivable frequency band, or in other words, the average value for the receivable frequency band.

Consequently, it is possible to select the optimal frequency with ease.

The biological sample measurement apparatus pertaining to the twelfth invention is the biological sample measurement apparatus pertaining to any of the first to eleventh inventions, wherein, if the receiver cannot properly receive the communication success signal even though the transmitter has sent the biological data, the transmitter resends the biological data with the transmission power set to maximum during transmission.

Here, in order to confirm that a shift in the communication frequency is not the cause of unsuccessful communication, the transmission power is increased to maximum while leaving the frequency band at the same setting as during transmission, and retransmission is performed.

Consequently, it is possible to avoid incidental unsuccessful communication caused by the effect of humans and so forth or the emission state of interfering radio waves in the surrounding environment.

With the biological sample measurement apparatus of the present invention, it is possible to attempt to establish communication by preferentially using a communication frequency with a higher probability of success in communication. Therefore, the time it takes until communication is successful can be shortened, and the emission of unnecessary radio waves can be reduced.

BRIEF DESCRIPTION OF DRAWINGS

FIG. 6 is a diagram illustrating an example of communication success history with the blood glucose level measurement apparatus in FIG. 3;

FIG. 13 is a diagram illustrating an example of a communication success table with the blood glucose level measurement apparatus in FIG. 11;

FIG. 15 is a communication frequency selection flowchart with the blood glucose level measurement apparatus in FIG. 14.

Figure 1:
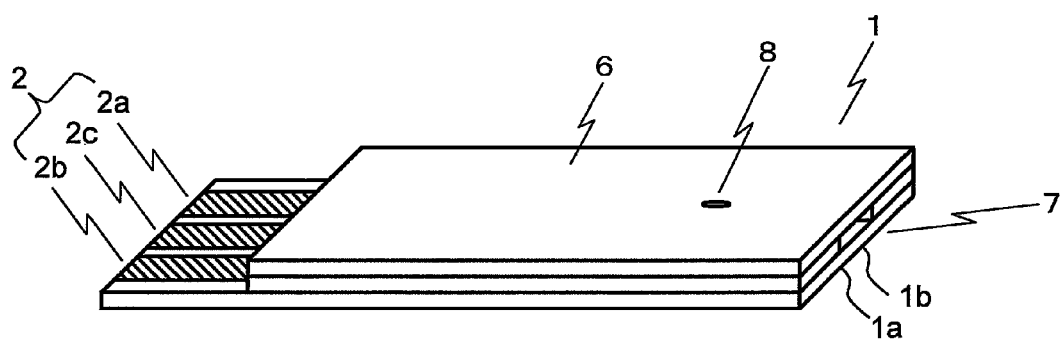
FIG. 1 is an oblique view of a test piece used in a blood glucose level measurement apparatus pertaining to a first embodiment of the present invention.

EXPLANATION OF REFERENCE CHARACTERS 1 test piece
2 electrode
2a electrode
2b electrode
2c electrode
3 insulated substrate
4 reagent layer
5 spacer
6 cover
7 specimen supply component
8 air hole
10 blood glucose level measurement apparatus (biological sample measurement apparatus)
11 test piece insertion component
11a insertion opening
11b contact electrode
12 measurement component (biological data measurement component)
12a connection electrode
12b reference voltage generation circuit
12c current-voltage conversion circuit
13 display component
14 transmitter
15 receiver
16 communication frequency setting component
17 transmission/reception switching component
18 storage component
19 communication frequency selector
20 controller
21 antenna
22 radio wave
23 portable terminal
30 measurement of blood glucose level
31 transmission data
32 transmission time
33 transmission processing
34 reply data
35 reception time
36 reception processing
37 reception period time
38 reception processing
39 transmission processing
40 reply data transmission period time
50 designed communication frequency (reference frequency)
51 frequency search interval
52 first communication frequency
53 second communication frequency
54 third communication frequency
60 blood glucose level measurement apparatus (biological sample measurement apparatus)
61 communication frequency selector
62 controller
70 blood glucose level measurement apparatus (biological sample measurement apparatus)
71 communication frequency selector
72 controller
73 ID input component (individual identification number input component)
156 first optimal frequency
160 search reference frequency
161 first communication attempt frequency
162 second communication attempt frequency
163 third communication attempt frequency
164 fourth communication attempt frequency
167 second optimal frequency

DETAILED DESCRIPTION OF THE INVENTION

An embodiment of the biological sample measurement apparatus of the present invention will now be described in detail through reference to the drawings.

Embodiment 1

Test Piece 1

First, the configuration of a test piece 1 used in a blood glucose level measurement apparatus (biological sample measurement apparatus) 10 of this embodiment, and the method for measuring a blood glucose level (biological data) will be described through reference to FIGS. 1 and 2.

Figure 2:
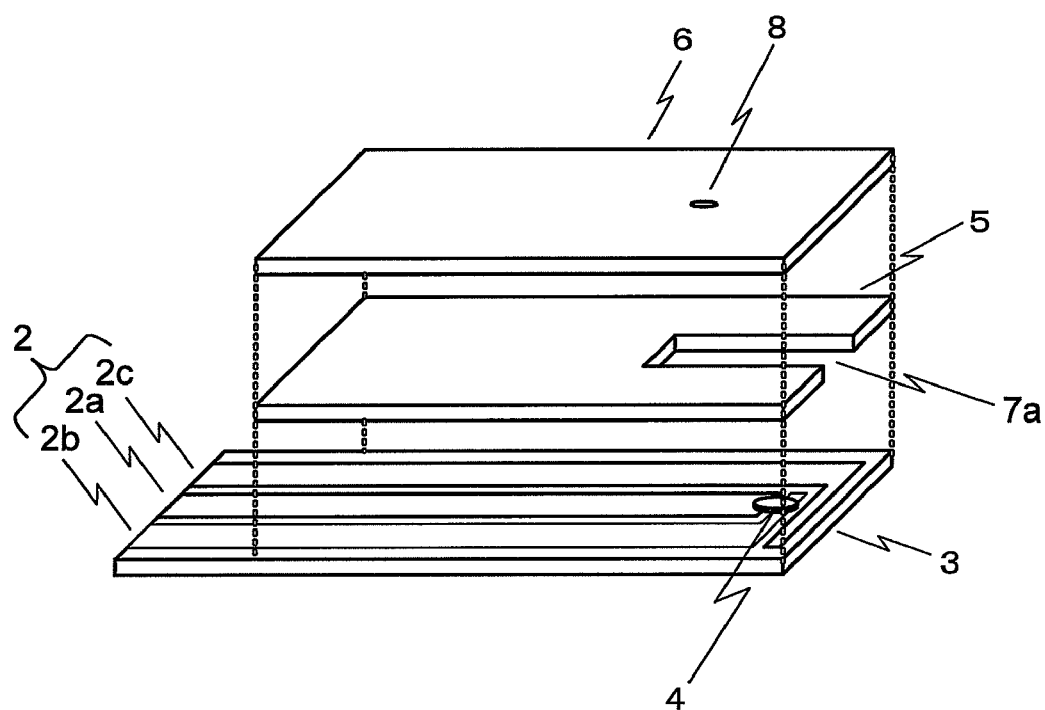
FIG. 2 is an exploded view of the internal configuration in FIG. 1.

As shown in FIGS. 1 and 2, the test piece 1 mainly comprises an electrode 2, an insulated substrate 3, a reagent layer 4, a spacer 5, a cover 6, a specimen supply component 7, and an air hole 8. The electrode 2 is equipped with three electrodes 2a, 2b, and 2c, each of which is formed on a face of the insulated substrate 3. The reagent layer 4, which includes a mediator and a oxidation-reduction enzyme such as a glucose dehydrogenase, is formed between the electrode 2a and the electrode 2b. The spacer 5 is affixed on the side of the insulated substrate 3 where the electrode is formed. A notch 7a that extends above at least the electrode 2a, the electrode 2b, and the electrode 2c is formed in the spacer 5. The cover 6 is further affixed to a face of the spacer 5, on the opposite side from the insulated substrate 3.

With this configuration, an opening 1b is formed at one end 1a of the test piece 1, and the specimen supply component 7 is formed including this opening 1b. The air hole 8 is provided to the portion of the cover 6 that overlaps the notch 7a. When a drop of blood is placed in the opening 1b which is included in the specimen supply component 7 and formed at one end 1a of the test piece 1, the blood fills the specimen supply component 7 through capillary action. Also, since the spacer 5 and the cover 6 are made shorter than the insulated substrate 3, the electrode 2 is exposed at the opposite end portion of the test piece 1 from the end portion where the opening 1b of the specimen supply component 7 is provided.

To measure a blood glucose level, first the test piece 1 is inserted into a blood glucose meter, the user checks that the blood glucose meter is in a state that allows measurement, and a drop of blood is placed in the opening of the specimen supply component 7. The drop of blood fills the specimen supply component 7 by capillary action, and when voltage is applied between the electrodes 2A and 2C, this filling is detected from a change in the current that flows between the electrodes.

Next, the blood filling the specimen supply component 7 is allowed to react with the reagent layer 4 for a specific length of time, after which voltage is applied between the electrode 2A (serving as a working electrode) and the electrode 2B (serving as a counter electrode), which oxidizes the mediator that is produced in a reduced state on the electrode 2A by the enzyme reaction, and current proportional to the amount of glucose is detected.

Next, voltage is applied between the electrode 2C (serving as a working electrode) and the electrode 2A (serving as a counter electrode), and current dependent on a Hct (hematocrit) value is detected on the basis of the electrolytic oxidation reaction of the blood component. Finally, the blood glucose level is measured by correcting the amount of glucose calculated from the current value with a Hct value that is also calculated from the current value.

Blood Glucose Level Measurement Apparatus 10

Figure 3:
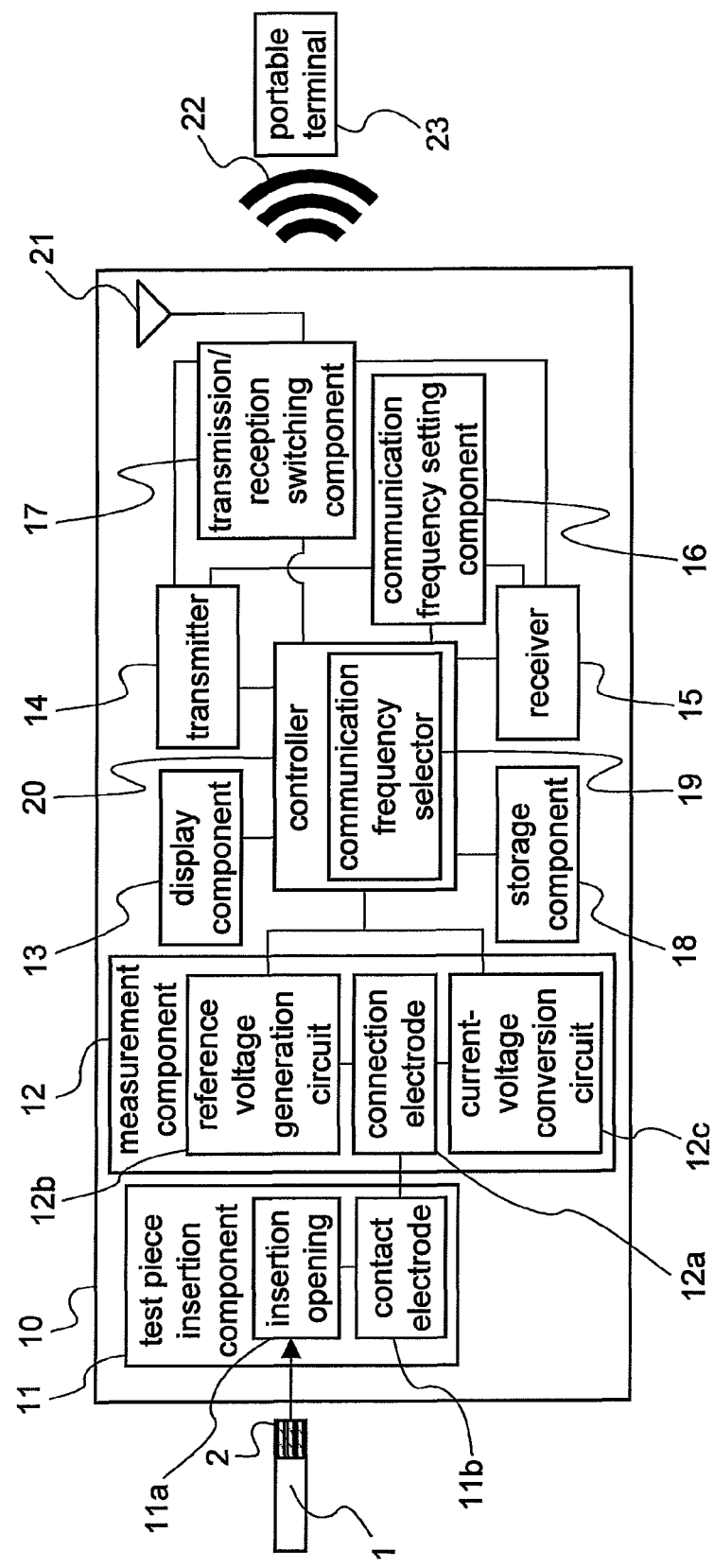
FIG. 3 is a block diagram of the configuration of the blood glucose level measurement apparatus pertaining to the first embodiment of the present invention.

Next, the configuration of the blood glucose level measurement apparatus 10 in this embodiment will be described through reference to FIG. 3. FIG. 3 is a block diagram of the configuration of the blood glucose level measurement apparatus 10. For the sake of convenience, a portable terminal 23, a radio wave 22, and the test piece 1 are also shown in FIG. 3 and in FIGS. 11 and 14 (discussed below).

The blood glucose level measurement apparatus 10 comprises a test piece insertion component 11 into which the test piece 1 is inserted, and a measurement component (biological data measurement component) 12 for measuring the blood glucose level of the user. It also comprises a display component 13 that allows the user to confirm the measured blood glucose level information, a transmitter 14 for wirelessly transmitting the measured blood glucose level information to the portable terminal 23, and a receiver 15 for wirelessly receiving a portable terminal ID (portable terminal individual identification number) sent from the portable terminal 23 and used to identify the portable terminal, and an acknowledge signal (communication success signal) indicating that communication is successful. It further comprises a communication frequency setting component 16 for setting the communication frequency at which communication is performed, a transmission/reception switching component 17 for switching between transmission and reception, a storage component 18 that stores various information, and a controller 20 that controls the various functions and includes a communication frequency selector 19 for selecting the communication frequency to be used in reception and transmission. It further comprises an antenna 21 that emits the radio wave 22 to the portable terminal 23.

The test piece insertion component 11 is provided with an insertion opening 11a for inserting the test piece 1, and a contact electrode 11b that comes into contact with the electrode 2 exposed on the test piece 1 when it has been inserted. The contact electrode 11b is connected to the electrode inside the measurement component 12 (hereinafter referred to as the connection electrode 12a).

The measurement component 12 is provided with the connection electrode 12a that connects to the contact electrode 11b of the test piece insertion component 11, a reference voltage generation circuit 12b that applies voltage to the connection electrode 12a, and a current-voltage conversion circuit 12c that converts a current value into a voltage value. The reference voltage generation circuit 12b is a D/A converter, for example, and applies voltage through the contact electrode 11b and the connection electrode 12a to the electrode 2A, the electrode 2B, and the electrode 2C for the sake of the electrolytic oxidation reaction of the blood component and the oxidation of the mediator, which are mentioned above. The current-voltage conversion circuit 12c is a circuit equipped with an operational amplifier and a feedback resistor, for example, and in order to detect current dependent on the Hct value on the basis of the above-mentioned electrolytic oxidation reaction of the blood component, a voltage signal corresponding to the value of the current flowing to the feedback resistor is converted by an A/D converter or the like into voltage value and detected, and the detected voltage value is sent to the controller 20.

The display component 13 is a liquid crystal monitor, for example, and displays time information, menu screens, and so forth in addition to measurement results.

The transmitter 14 performs the encoding of the transmission data including blood glucose level information measured by the measurement component 12, the adding of error detection codes, and modulation by using the communication frequency set with the communication frequency setting component 16, and supplies a modulation signal through the transmission/reception switching component 17 to the antenna 21, which is emitted as the radio wave 22 from the antenna 21.

A radio wave (modulated signal) received by the antenna 21 is inputted to the receiver 15 through the transmission/reception switching component 17, and this modulated signal is demodulated by using the communication frequency set with the communication frequency setting component 16. After this, error detection processing and encoding processing are performed, and received data including the portable terminal ID and the acknowledge signal is produced.

The communication frequency setting component 16 sets the communication frequency selected by the communication frequency selector 19 in the transmitter 14 and the receiver 15. The frequency band that is used is, for example, the short-range wireless frequency band allotted to medical use and called the ISM band.

The transmission/reception switching component 17 is a change-over switch, for example, and performs switching for selecting either the transmission or the reception of data. When data is to be sent, the modulated signal produced by the transmitter 14 is sent to the antenna 21, and the antenna 21 emits this modulated signal as the radio wave 22. On the other hand, when data outputted from the portable terminal 23 is to be received, the modulated signal received by the antenna 21 is sent to the receiver 15, and received data is produced.

The storage component 18 is a nonvolatile memory, for example, and holds blood glucose level information measured in the past, the success/failure history of past wireless communication, communication frequencies that are successful in wireless communication in the past, portable terminal ID's, and so forth. Communication frequencies with which there is successful communication in the past are stored as communication success history in association with the portable terminal ID received at this time, which will be discussed in detail at a later time.

The controller 20 is a microcomputer, for example, and controls the various functions of the display component 13, the transmitter 14, the receiver 15, the communication frequency setting component 16, the transmission/reception switching component 17, and the storage component 18, and calculates blood glucose levels according to voltage values sent from the measurement component 12.

The communication frequency selector 19 provided in the controller 20 selects a communication frequency from among the communication success history stored in the storage component 18, and sends the selected communication frequency to the communication frequency setting component 16. The specific method for selecting the communication frequency will be described in detail below.

Portable Terminal 23

The portable terminal 23 will now be described, which is what communicates with the blood glucose level measurement apparatus in this embodiment. The portable terminal 23 has the functions of storing blood glucose level data measured by the blood glucose level measurement apparatus 10 and displaying it as a graph, analyzing indexes, and transferring the blood glucose level data through a network to a medical facility or the like. Upon receiving the blood glucose level data from the blood glucose level measurement apparatus 10, the portable terminal 23 sends the blood glucose level measurement apparatus 10 the acknowledge signal indicating that communication is successful, and the internally held portable terminal ID for identifying the portable terminal 23.

Communication Between Blood Glucose Level Measurement Apparatus 10 and Portable Terminal 23

Figure 4:
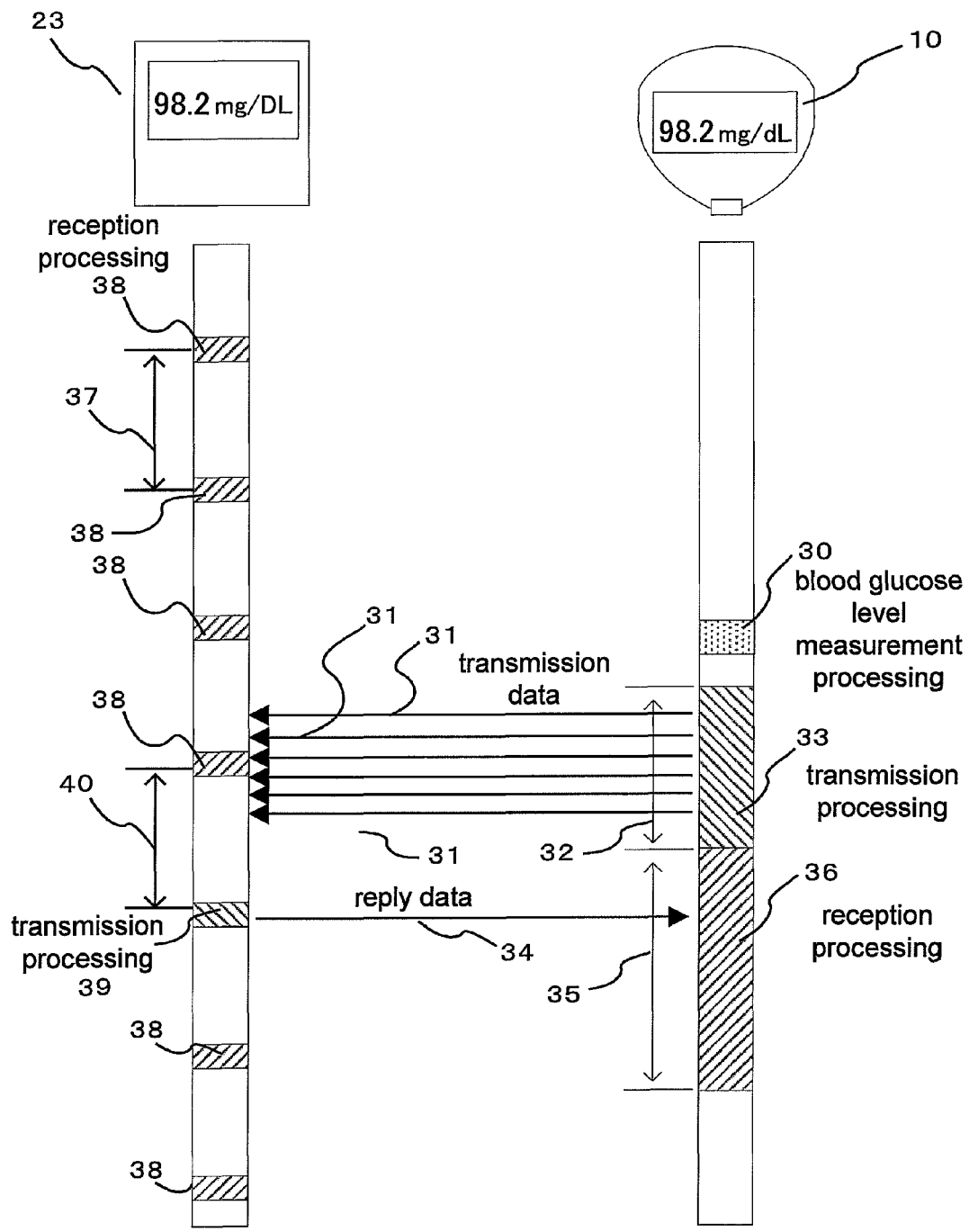
FIG. 4 is a sequence diagram of wireless communication between a portable terminal and the blood glucose level measurement apparatus in FIG. 3.

Next, the method of communication between the blood glucose level measurement apparatus 10 and the portable terminal 23 will be described through reference to FIG. 4. FIG. 4 is a sequence diagram of communication between the blood glucose level measurement apparatus 10 and the portable terminal 23.

The blood glucose level measurement apparatus 10 performs measurement processing 30 of a user's blood glucose level, after which it performs transmission processing 33 for a specific transmission time 32 (3 seconds, for example) to send transmission data 31 including the measured blood glucose level information to the portable terminal 23, and during the transmission processing 33, sends the transmission data 31 intermittently a plurality of times. The transmission data 31 that is sent here is the blood glucose level measured by the blood glucose level measurement apparatus 10, the serial number of the blood glucose level measurement apparatus 10, the measurement time and date, data for detecting errors in the transmission data, and so forth.

Also, after performing the transmission processing 33, the blood glucose level measurement apparatus 10 performs reception processing 36 for a specific reception time 35 (4 seconds, for example) to receive reply data 34 from the portable terminal 23. The reply data 34 received here is the acknowledge signal for notifying of successful communication (the completion of reception), the portable terminal ID unique to each individual portable terminal 23, and so forth. In the reception processing 36, if the acknowledge signal included in the reply data 34 from the portable terminal 23 cannot be received, the communication frequency is changed and the transmission processing 33 and reception processing 36 are performed again, which is repeated until an acknowledge signal can be received.

Meanwhile, the portable terminal 23 performs reception processing 38 to receive blood glucose level information at every specific period (hereinafter referred to as the reception period time 37). Since the reception period time 37 is set to a shorter period time (2.5 seconds, for example) than the transmission time 32 of the blood glucose level measurement apparatus 10, the reception processing 38 of the portable terminal 23 will always be executed once within the transmission time 32 of the blood glucose level measurement apparatus 10. If the transmission data sent by the blood glucose level measurement apparatus 10 can be properly received in the reception processing 38 of the portable terminal 23, the reply data 34 is produced, and the reply data 34 is sent during the transmission processing 39 after a specific amount of time (hereinafter referred to as the reply data transmission period time 40) has elapsed since the receipt of the transmission data 31.

The reply data transmission period time 40 is set to a longer time (3.2 seconds, for example) than the transmission time 32 of the blood glucose level measurement apparatus 10, so when the reply data 34 is sent from the portable terminal 23, the reply data 34 can always be received in the reception processing 36 of the blood glucose level measurement apparatus 10 having a wireless communication function.

Method for Selecting Communication Frequency in Blood Glucose Level Measurement Apparatus 10

Figure 5:
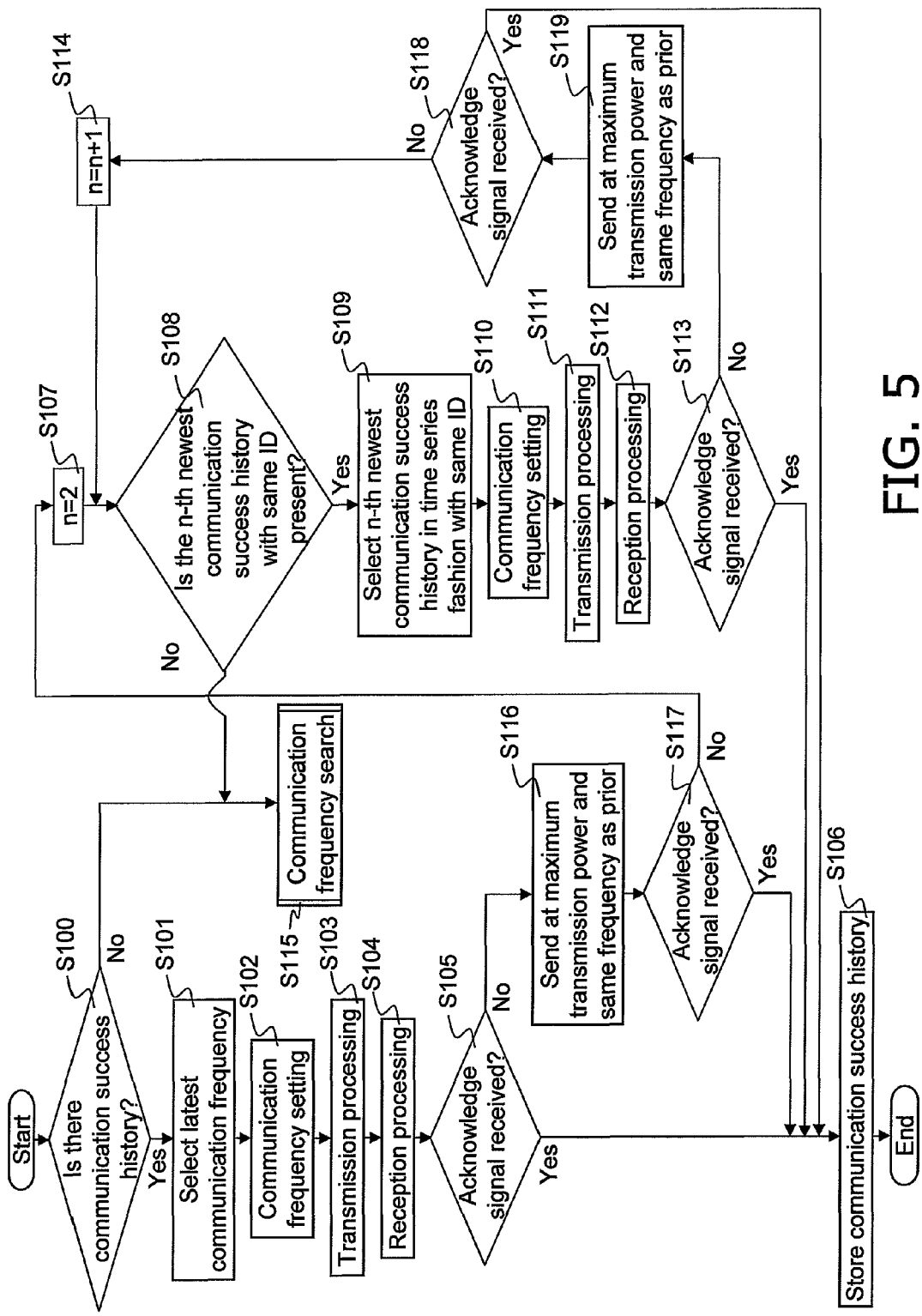
FIG. 5 is a communication frequency selection flowchart with the blood glucose level measurement apparatus in FIG. 3.
Figure 7:
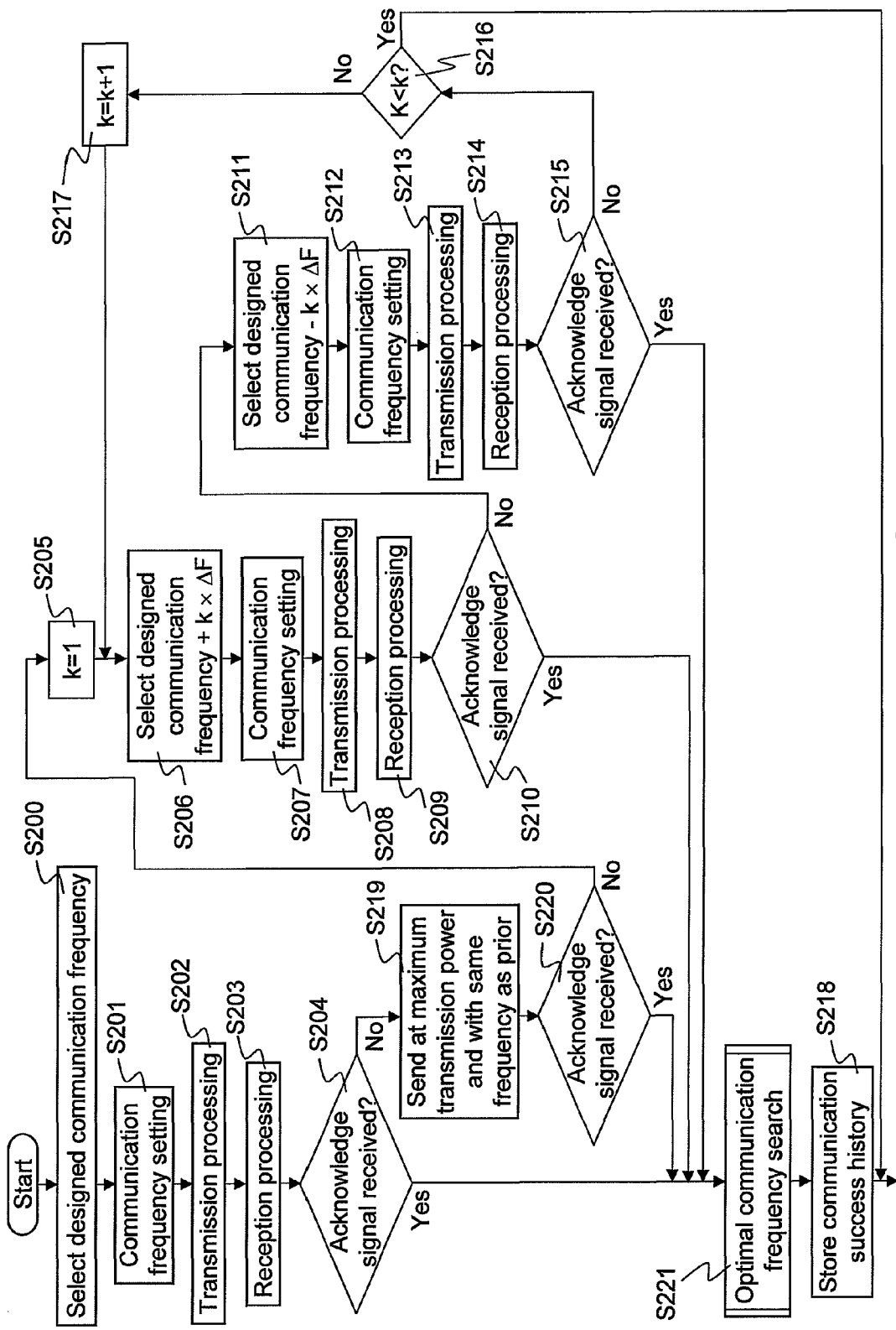
FIG. 7 is a flowchart of searching for a communication frequency with the blood glucose level measurement apparatus in FIG. 3.
Figure 8:
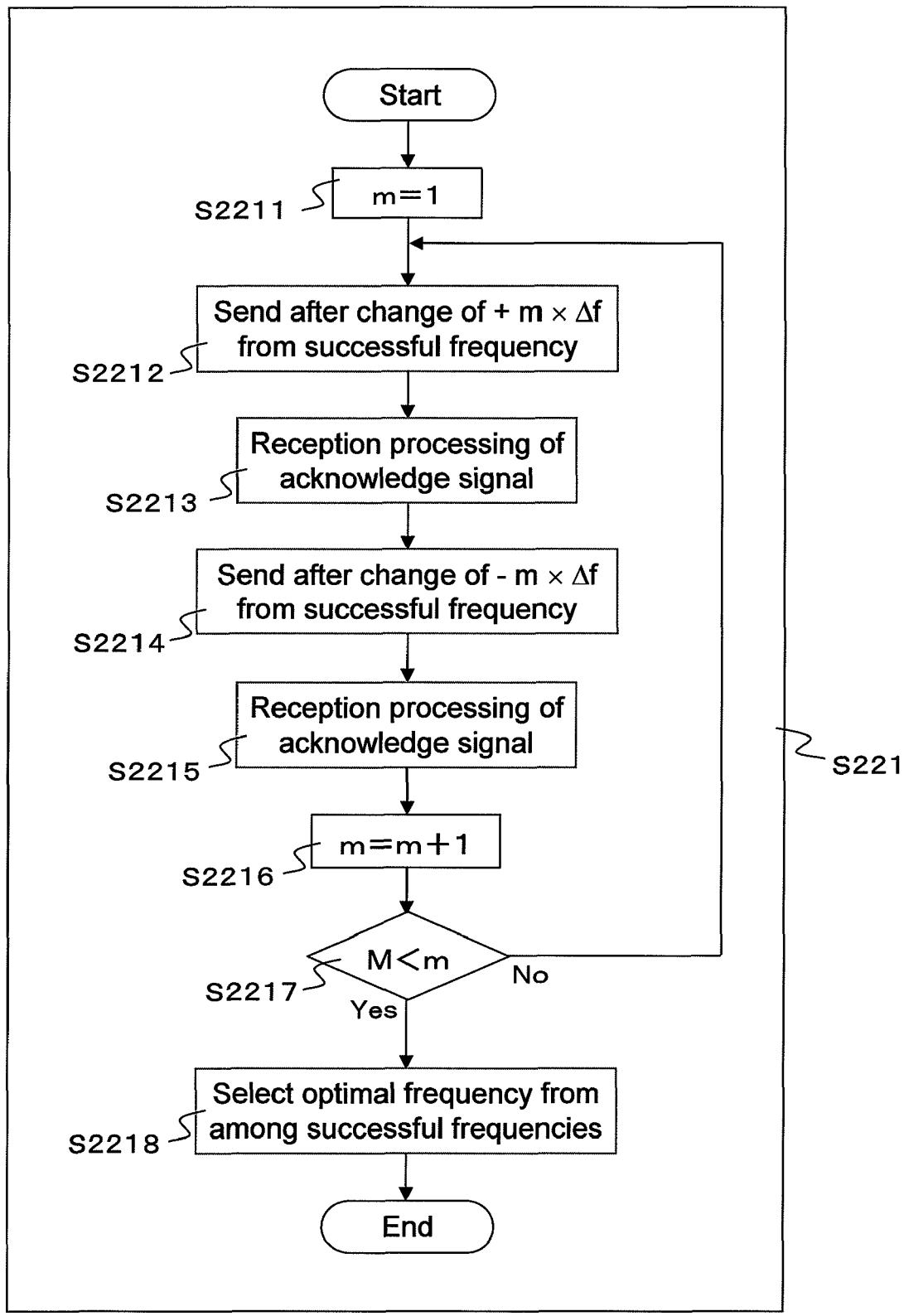
FIG. 8 is a flowchart illustrating the details of S221 in the flowchart of FIG. 7.
Figure 9:
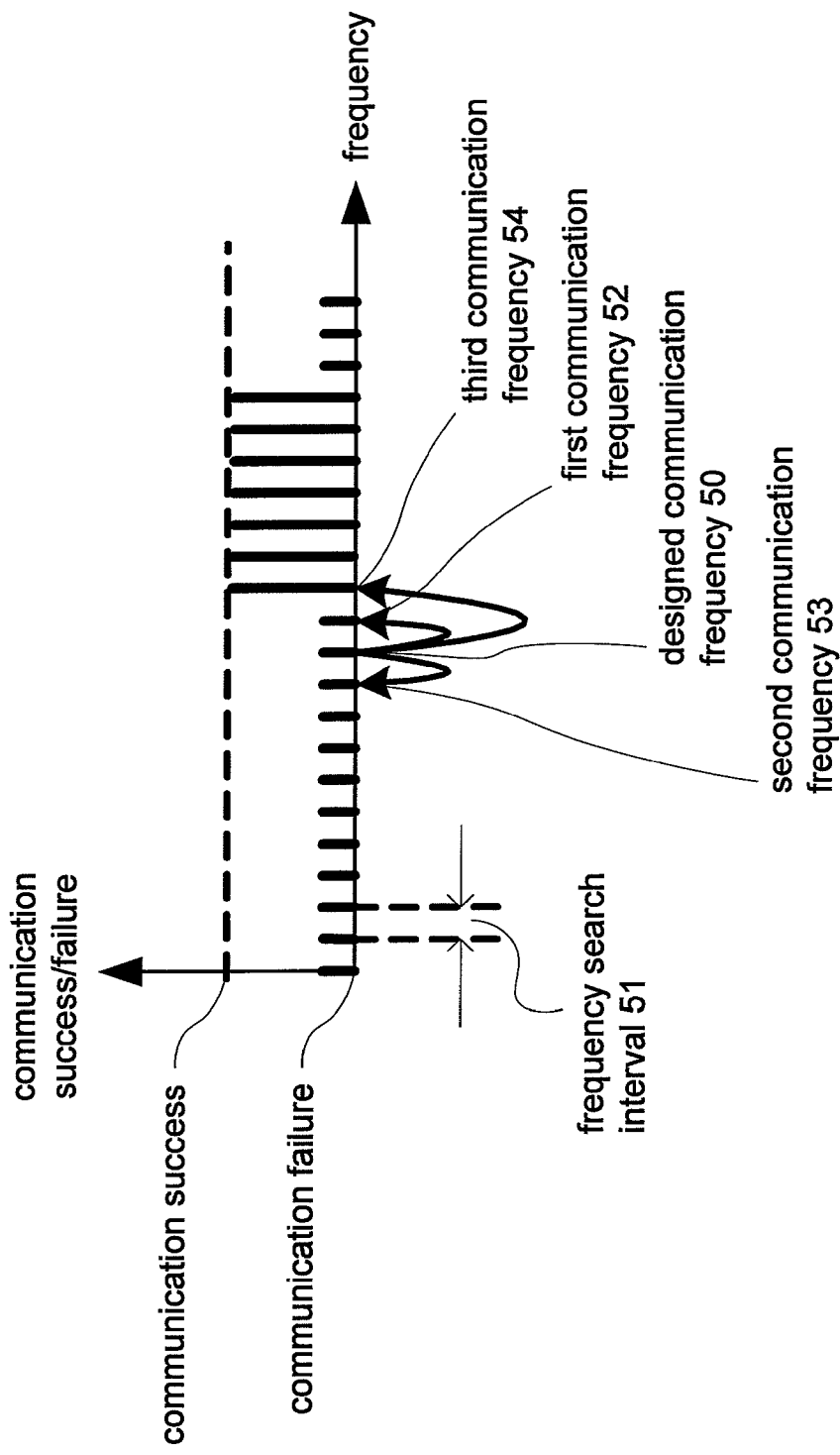
FIG. 9 is a concept diagram illustrating a method for searching for a communication frequency with the blood glucose level measurement apparatus in FIG. 3.
Figure 10:
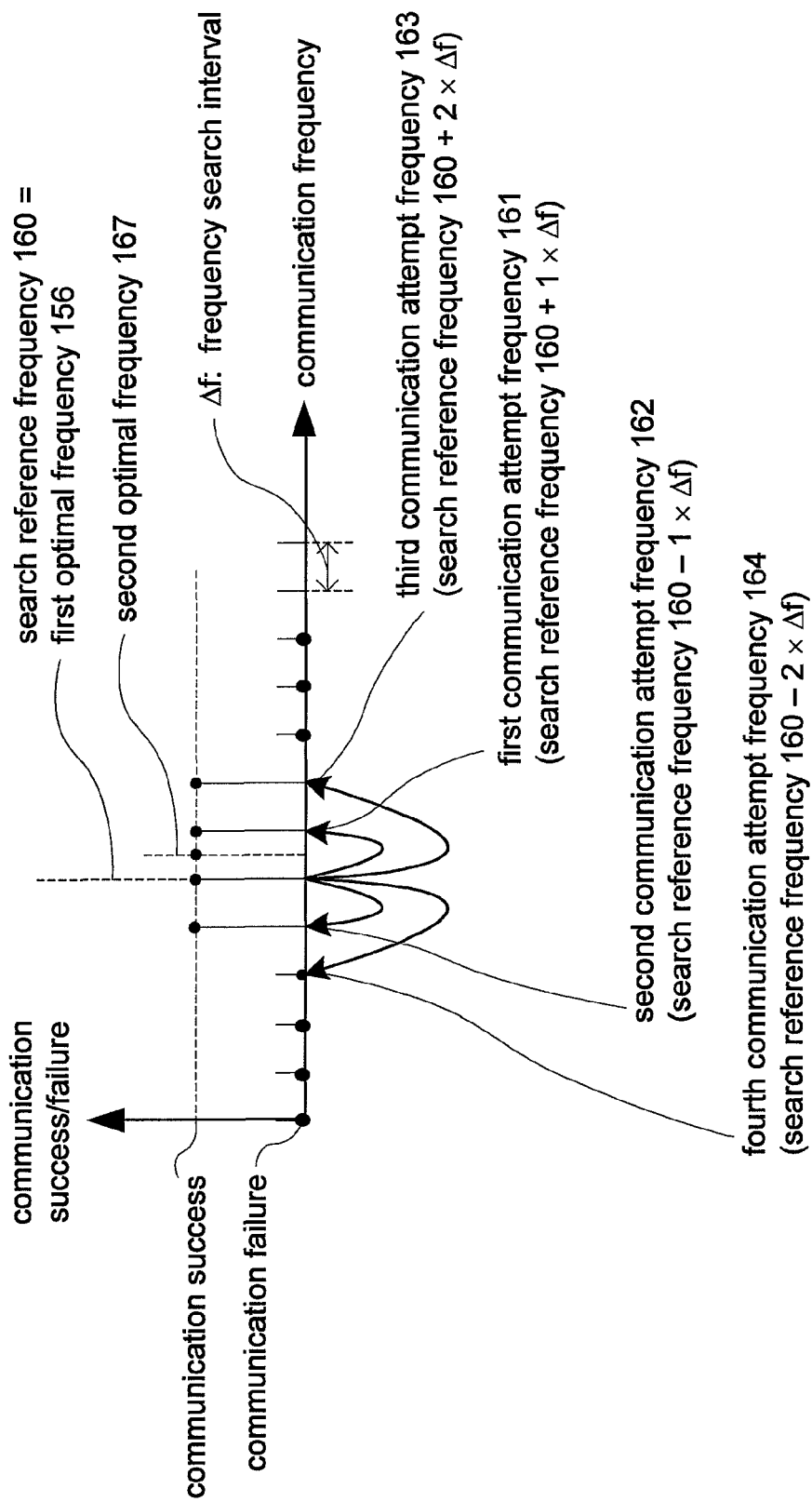
FIG. 10 is a schematic diagram of the method for searching for a second optimal frequency.

Next, the method for selecting the communication frequency performed by the communication frequency selector 19 of the blood glucose level measurement apparatus 10 of this embodiment, and the communication success history stored in the storage component 18 will be described through reference to FIGS. 5 to 10. FIGS. 5, 7, and 8 are flowcharts of the method for selecting the communication frequency performed by the communication frequency selector 19 of the blood glucose level measurement apparatus 10 in this embodiment. FIG. 6 shows an example of the communication success history stored in the storage component 18, while FIGS. 9 and 10 are concept diagrams of a communication frequency search method.

First, in FIG. 5, when communication is commenced, in step S100 the communication frequency selector 19 confirms whether or not a communication success history is present in the storage component 18. The communication success history referred to here is a communication frequency and a portable terminal ID stored when communication is successful in the past, and is as shown in FIG. 6, for example. Specifically, whenever communication is successful, the portable terminal ID is associated with the communication frequency, and this set of information is stored. FIG. 6 shows the history for 16 times, from DATA0 to DATA15, and the history is past information moving from DATA0 toward DATA15. In this set of information, the communication frequency is shown at the top, and the portable terminal ID below. The numerical values shown in FIG. 6 are just examples, and the history that is stored is not limited to 16 times.

If even one communication success history is present in step S100, that is, if communication has been successful even once in the past, the flow moves on to step S101, but if there is not a single communication success history, that is, if there is not even a single communication in the past, or if it never succeeds though the establishment of communication has been tried, the flow moves on to step S115. For instance, a communication success history is present in the example shown in FIG. 6, so the flow moves on to step S101. From here on, we will describe an example in which the communication success history shown in FIG. 6 is stored in the storage component 18.

Then, in step S101, the communication frequency selector 19 selects a latest communication frequency from among the communication success history stored in the storage component 18. The "latest communication frequency" referred to here means the most recent communication frequency for which communication is successful between the blood glucose level measurement apparatus 10 and the portable terminal 23, and in FIG. 6, for example, since DATA0 is the most recent data, the latest communication frequency is 2.44 GHz.

In step S102, the communication frequency setting component 16 receives the value of the communication frequency selected by the communication frequency selector 19, and the communication frequency setting component 16 conveys the value of the communication frequency to the transmitter 14 and the receiver 15. The transmitter 14 then performs modulation processing by using the communication frequency set by the communication frequency setting component 16, and the receiver 15 performs demodulation processing by using the communication frequency set by the communication frequency setting component 16.

In step S103, the controller 20 issues a command to the transmission/reception switching component 17 to switch to the transmission direction, and performs the transmission processing 33 by sending a transmission command to the transmitter 14. The transmitter 14 supplies the modulated signal through the transmission/reception switching component 17 to the antenna 21, which is emitted as the radio wave 22 from the antenna 21.

In step S104, the controller 20 issues a command to the transmission/reception switching component 17 to switch to the reception direction, and performs the reception processing 36 by sending a reception command to the receiver 15.

In step S105, the receiver 15 analyzes the received data received through the antenna 21 and the transmission/reception switching component 17, and confirms whether or not there is an acknowledge signal. If an acknowledge signal has been received from the portable terminal 23 in the reception processing 36, it is determined that communication is successful and the flow moves on to step S106, but if no acknowledge signal is received from the portable terminal 23, it is determined that communication failed, and the flow is moved to step S116.

In step S116, the transmission processing 33 is performed at the maximum transmission power and with the same communication frequency left the same. This is performed in order to check whether the cause of the communication failure in the transmission processing 33 of step S103 occurs not by a deviation in the communication frequency, but by the effect of humans or the emission state of interfering radio waves in the surrounding environment and so forth.

In step S117, it is determined whether or not communication is successful at the maximum transmission power setting and at the communication frequency in step S116. The determination in step S117 is made by the same method as in step S105 discussed above. If communication is deemed successful, the flow moves on to step S106, but if it is deemed unsuccessful, the flow moves on to step S107.

First, the description will proceed from step S107 for a case when no acknowledge signal could be received, and step S106 will be discussed later.

In step S107, the value of the communication frequency selection count n is set to 2. The communication frequency selection count n is related to processing for selecting the communication frequency from the communication success history in subsequent steps S108 and S109.

In step S108, the communication frequency selector 19 confirms whether an n-th newest communication success history in time series order is present, with the same portable terminal ID as in the prior communication (labeled as same ID in the flowchart), from among the communication success history stored in the storage component 18. If one is present, the flow proceeds to step S109, and if not, to step S115. First, when n=2, the prior communication is the communication using the DATA0 in FIG. 6 selected in step S101, and the same portable terminal ID as in the prior communication is the ID2 of DATA0. Therefore, in FIG. 6, the communication success history for the second newest ID2 in time series order is DATA2, and since it is present in the communication success history, the flow proceeds to step S109. Step S115 will be described in detail below, through reference to FIG. 7.

In step S109, the communication frequency selector 19 selects the n-th newest communication success history in time series order, with the same portable terminal ID as the prior communication, as the communication frequency from among the communication success history stored in the storage component 18. As discussed above, since the communication success history of the second newest ID2 in time series order is DATA2, the DATA2 communication success frequency of 2.43 GHz is selected here as the communication frequency when n=2.

Steps S110 to S113 are substantially the same as the above-mentioned steps S102 to S105, but the communication frequency set in step S110 is different from that in step S102. Also, in step S113, if it is determined that an acknowledge signal has been received, the flow proceeds to step S106, but if it is determined that none has been received, the flow proceeds to step S119.

In step S119, the transmission processing 33 is performed at the maximum transmission power and with the communication frequency left the same. This is performed in order to check whether the cause of the communication failure in the transmission processing 33 of step S111 occurs not by a deviation in the communication frequency, but by the effect of humans or the emission state of interfering radio waves in the surrounding environment and so forth.

In step S118, it is determined whether or not communication is successful at the maximum transmission power setting and at the communication frequency in step S119. The determination in step S118 is made by the same method as in step S105 discussed above. If communication is deemed successful, the flow moves on to step S106, but if it is deemed unsuccessful, the flow moves on to step S114.

Let us assume here that no acknowledge signal could be received, and first describe from step S114. Step S106 will be described below.

In step S114, 1 is added to the value of the communication frequency selection count n, and the communication frequency selected from among the communication success history in step S109 is changed.

Then, the flow goes back to step S108, and it is confirmed whether an n-th newest communication success history in time series order is present, with the same portable terminal ID as in the prior communication, from among the communication success history. When n=3, the communication frequency in DATA2 is used in the prior communication, so the third newest communication success history with the same portable terminal ID as in DATA2 is DATA5.

Subsequently, the same processing as that described for steps S108 to S114 is repeated, thereby attempting to establish communication while increasing the value of n until there is no n-th history and changing the communication frequency. Even if communication is attempted until the is no more history, if no acknowledge signal can be confirmed from the portable terminal 23, the flow goes to step S115. In this embodiment, DATA14 is the last history with the same portable terminal ID, and if no acknowledge signal can be confirmed from the portable terminal 23 even when the communication success history of DATA14 is used, the flow goes to step S115.

The operation in step S106 when an acknowledge signal has been received will now be described. In step S106, the portable terminal ID and communication frequency included in the received reply data 34 are written as communication success history to the storage component 18. In the case of FIG. 6, the newest communication success history is written to DATA0, and other histories are shifted toward the past. If there is no more room to record history in the storage component, the oldest history is deleted.

Communication Frequency Search Method

The communication frequency search method of step S115 will now be described through reference to FIGS. 7, 8, 9, and 10.

The communication frequency search of step S115 is executed when no communication frequency at which communication is possible is present in the communication success history. A new communication frequency not present in the communication success history is searched for, and communication is performed using the retrieved communication frequency.

In the flowchart of FIG. 7, first, in step S200, a designed communication frequency is selected as the first communication frequency. Here, the designed communication frequency (hereinafter sometimes referred to as a reference frequency) is a communication frequency predetermined between the blood glucose level measurement apparatus 10 and the portable terminal 23, and is a short-range wireless frequency allotted to medical use and called the ISM band. For example, 2.45 GHz is set as the reference frequency.

Next, step S201 is carried out in the same manner as in step S102 shown in FIG. 5, step S202 as in step S103 shown in FIG. 5, and step S203 as in step S104 shown in FIG. 5, and transmission and reception processing are performed using the reference frequency (an attempt is made to establish communication).

In step S204, just as in step S105 shown in FIG. 5, if an acknowledge signal has been received from the portable terminal 23, it is determined that communication is successful and the flow proceeds to step S221 (see FIG. 8), but if no acknowledge signal has been received from the portable terminal 23, it is determined that communication failed, and the flow moves to step S219.

In step S219, the transmission processing 33 is performed at the maximum transmission power with the communication frequency left the same. This is performed in order to check whether the cause of the communication failure in the transmission processing 33 of step S202 occurs not by a deviation in the communication frequency, but by the effect of humans or the emission state of interfering radio waves in the surrounding environment and so forth.

In step S220, it is determined whether or not communication is successful at the maximum transmission power setting and at the communication frequency in step S219. The determination in step S220 is made by the same method as in step S105 discussed above. If communication is deemed successful, the flow moves on to step S221, but if it is deemed unsuccessful, the flow moves on to step S205.

In step S205, the value of the communication frequency search count k is set to 1. The communication frequency search count k is related to processing for selecting a new communication frequency in subsequent steps S206 and S211.

In steps S206 and S211, the communication frequency is changed. A search for a communication frequency with which communication is possible is then performed by the loop processing of steps S206 to S217. The method for searching for a communication frequency with which communication is possible will now be described on the basis of FIG. 9.

In FIG. 9, the vertical axis is communication success or failure, and the horizontal axis is the frequency value in communication. In searching for a communication frequency with which communication is possible, the communication frequency selector 19 uses the designed communication frequency 50 as a reference and selects a communication frequency that has been shifted by a specific frequency width ($\pm k \times \Delta F$). The selected communication frequency is then used to perform the transmission processing 33. In the reception processing 36 with respect to this transmission processing 33, whether or not the transmission processing 33 is successful, that is, whether or not communication is successful, is determined by checking for an acknowledge signal. This processing is repeated while the communication frequency is changed (while the value of k is changed as 0, 1, 2, ... ). FIG. 9 shows that the transmission processing 33 failed at the first communication frequency 52 (reference frequency+1×ΔF) and the second communication frequency 53 (reference frequency−1×ΔF) at k=1, and the transmission processing 33 succeeded at the third communication frequency 54 (reference frequency+2×ΔF) at k=2, and thereby a communication frequency at which communication is possible could be found. ΔF (a frequency search interval 51) is 10 MHz in this embodiment, but is not limited to this value. The above-mentioned reference frequency and the frequency search interval (ΔF) are stored ahead of time in the storage component.

When k=1, the first communication frequency 52 (the reference frequency (which is 2.45 GHz here)+1×ΔF (which is 10 MHz here)) is selected as the communication frequency (step S206), the setting of the selected communication frequency is performed (step S207), and then the transmission processing 33 is performed (step S208). The reception processing 36 is then performed with respect to the transmission processing 33 (step S209), and it is determined whether or not the transmission processing 33 is successful (step S210). As a result, if an acknowledge signal could not be received, the flow proceeds to step S211 and the search continues for a communication frequency, but if an acknowledge signal is received, the flow proceeds to step S221.

Then, in step S210, if no acknowledge signal is received, k is similarly set to 1, the second communication frequency 53 (the reference frequency−1×ΔF) is selected as the communication frequency (step S211), the setting of the selected communication frequency is performed (step S212), and then the transmission processing 33 is performed (step S213). The reception processing 36 is then performed with respect to the transmission processing 33 (step S214), and it is determined whether or not the transmission processing 33 is successful (step S215). As a result, if an acknowledge signal could not be received, the flow proceeds to step S216 and the search continues for a communication frequency, but if an acknowledge signal is received, the flow proceeds to step S221.

Then, if no acknowledge signal is received in step S215, it is determined in step S216 whether or not a value of the communication frequency search count k exceeds a value of the search count limit K (such as 10 times) that is set. If the value of the preset search count limit K has not been exceeded here, that is, if communication failed but the transmission processing 33 has not been performed the specified number of times, 1 is added to the communication frequency search count k in step S217, and the flow goes back to step S206. On the other hand, if the value of the preset search count limit K has been exceeded, that is, if communication has not been successful even though transmission has been performed by changing the communication frequency the specified number of times, the frequency search processing is ended.

The method for searching for a optimal communication frequency in step S221 will be described in detail here through reference to FIG. 8.

In step S2211, the second communication attempt count m is initialized to 1. The second communication attempt count m here is related to the communication frequency in wireless communication in steps S2212 and 2214.

In steps S2212 and 2214, the transmission processing 33 is performed by using the frequency at which communication is successful (first optimal frequency 156) in step S208 or step S213 as a reference, and changing it by a specific frequency width ($\pm k \times \Delta f$). In steps S2213 and 2215, the reception processing 36 is performed for an acknowledge signal with respect to the transmission processing 33 in steps S2212 and 2214. In steps S2213 and 2215, whether or not the communication is successful is stored in the storage component 18. Δf is set to a value less than the above-mentioned ΔF, such as 50 kHz.

In step S2216, 1 is added to the value of the second communication attempt count m. In step S2217, it is determined whether or not the second communication attempt count m exceeds the value of a preset specified count (such as 2 times). If the value of the preset specified count M has not been exceeded, the flow goes back to step S2212. On the other hand, if the preset second communication attempt count m does exceed the value of the specified count M, the optimal frequency (hereinafter referred to as the second optimal frequency 167) is selected from among the frequencies that are successful in steps S2212 to S2215 (the receivable frequency band).

Consequently, by selecting the second optimal frequency 167 from the receivable frequency band, it is possible to control to a frequency band that is more favorable than the above-mentioned first optimal frequency 156.

Changes to the frequency width will now be summarized through reference to FIG. 10.

In FIG. 10, a search reference frequency 160 corresponds to the frequency (the first optimal frequency 156) at which communication is successful in step S208 or step S213, and first, if m=1, the transmission processing 33 is attempted at the first communication attempt frequency 161 (a frequency of the search reference frequency 160+1×Δf) of step S2212. Then in the reception processing 36 of step S2213, it is determined whether or not the transmission processing 33 is successful in step S2212. FIG. 10 shows that wireless communication is successful at the first communication attempt frequency 161 (a frequency of the search reference frequency 160+1×Δf) of step S2212 and m=1, wireless communication is successful at the second communication attempt frequency 162 (a frequency of the search reference frequency 160−1×Δf) of step S2214 and m=1, wireless communication is successful at the third communication attempt frequency 163 (a frequency of the search reference frequency 160+2×Δf) of step S2212 and m=2, and wireless communication failed at the fourth communication attempt frequency 164 (a frequency of the search reference frequency 160−2×Δf) and m=2.

In step S2218, the second optimal frequency 167 is calculated based on the range of frequency over which wireless communication is successful in steps S2214 and 2215, that is, the receivable frequency band. In FIG. 10, the range of frequency over which wireless communication is successful is the range from the second communication attempt frequency 162 to the third communication attempt frequency 163, and the frequency in the middle of this range is calculated as the second optimal frequency 167. M is preferably a value that thoroughly encompasses the range of frequency over which communication is successful, taking into account such things as the performance of the various parts, such as the receiver 15 and the transmitter 14, and the initial settings of the apparatus.

In step S218, which is executed if an acknowledge signal is received in step S204, S210, or S215, the communication frequency and the portable terminal ID included in the received reply data 34 are stored as communication success history in the storage component 18 only if the search for a communication frequency is successful, that is, if communication is successful.

As discussed above, in this embodiment, transmission is first performed using the latest communication success frequency, referring to the communication success history stored in the storage component 18, and if communication is impossible, a communication frequency associated with the same portable terminal ID as the latest communication success frequency is selected while going back in time from the present in time series order, communication is performed using the selected communication frequency, and if communication is still impossible, a search is made for a new communication frequency, so that a communication frequency at which communication is possible can be set in fewer steps.

Also, since a single user generally uses a specific portable terminal, selecting the communication frequency stored in association with the same portable terminal ID in time series order from the newest to the oldest is particularly effective at reducing how long it takes to establish communication and cutting down on unnecessary radio waves.

Embodiment 2

Figure 11:
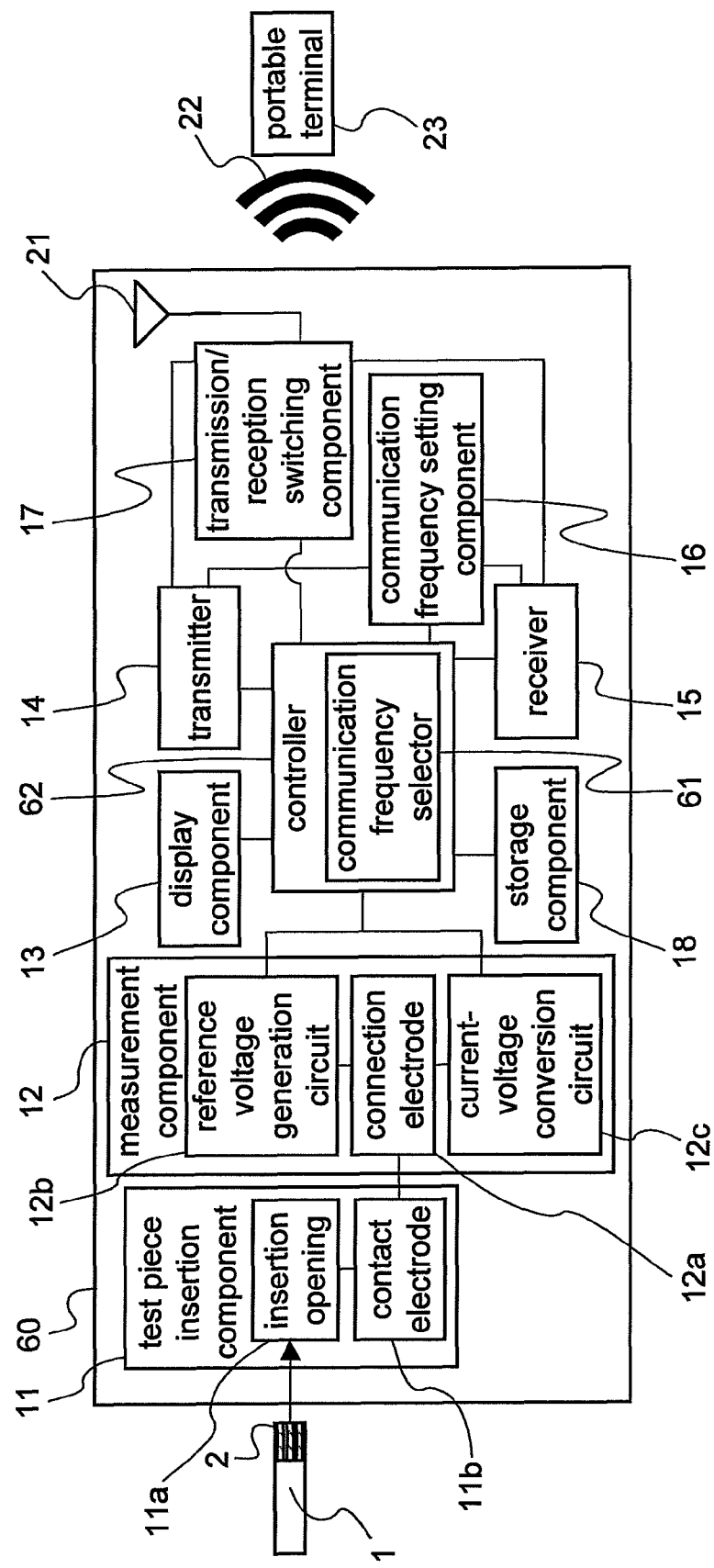
FIG. 11 is a block diagram of the configuration of a blood glucose level measurement apparatus pertaining to a second embodiment of the present invention.

Next, the configuration of a biological sample measurement apparatus in another embodiment of the present invention will be described through reference to FIG. 11. FIG. 11 is a block diagram of the configuration of a blood glucose level measurement apparatus in this embodiment. Components that have the same configuration as described in Embodiment 1 and shown in FIG. 3 are numbered the same and will not be described again.

In FIG. 11, a blood glucose level measurement apparatus 60 comprises a test piece insertion component 11 into which the test piece 1 is inserted, a measurement component 12 for measuring the blood glucose level of the user, a display component 13 that allows the user to confirm the measured blood glucose level information, a transmitter 14 for wirelessly transmitting the measured blood glucose level information to a portable terminal 23, a receiver 15 for wirelessly receiving a portable terminal ID sent from the portable terminal 23 and used to identify the portable terminal and an acknowledge signal indicating that communication is successful, a communication frequency setting component 16 for setting the communication frequency at which transmission/reception is performed, a transmission/reception switching component 17 for switching between transmission and reception, a storage component 18 that stores various information, a controller 62 that controls the various functions and includes a communication frequency selector 61 for selecting a communication frequency at which communication is possible, and an antenna 21 that emits a radio wave 22 to the portable terminal 23.

The test piece insertion component 11 includes an insertion opening 11a and a contact electrode 11b, and the measurement component 12 includes a connection electrode 12a, a reference voltage generation circuit 12b, and a current-voltage conversion circuit 12c.

The difference from the blood glucose level measurement apparatus of the first embodiment shown in FIG. 3 is the method for selecting the communication frequency performed by the communication frequency selector 61. With the communication frequency selector 61 in this embodiment, a communication success count is found for each portable terminal ID from the communication success history stored in the storage component 18, and the selection of the communication frequency is performed on the basis of the communication success count thus found.

Communication Frequency Selection Method of Blood Glucose Level Measurement Apparatus 60

Figure 12:
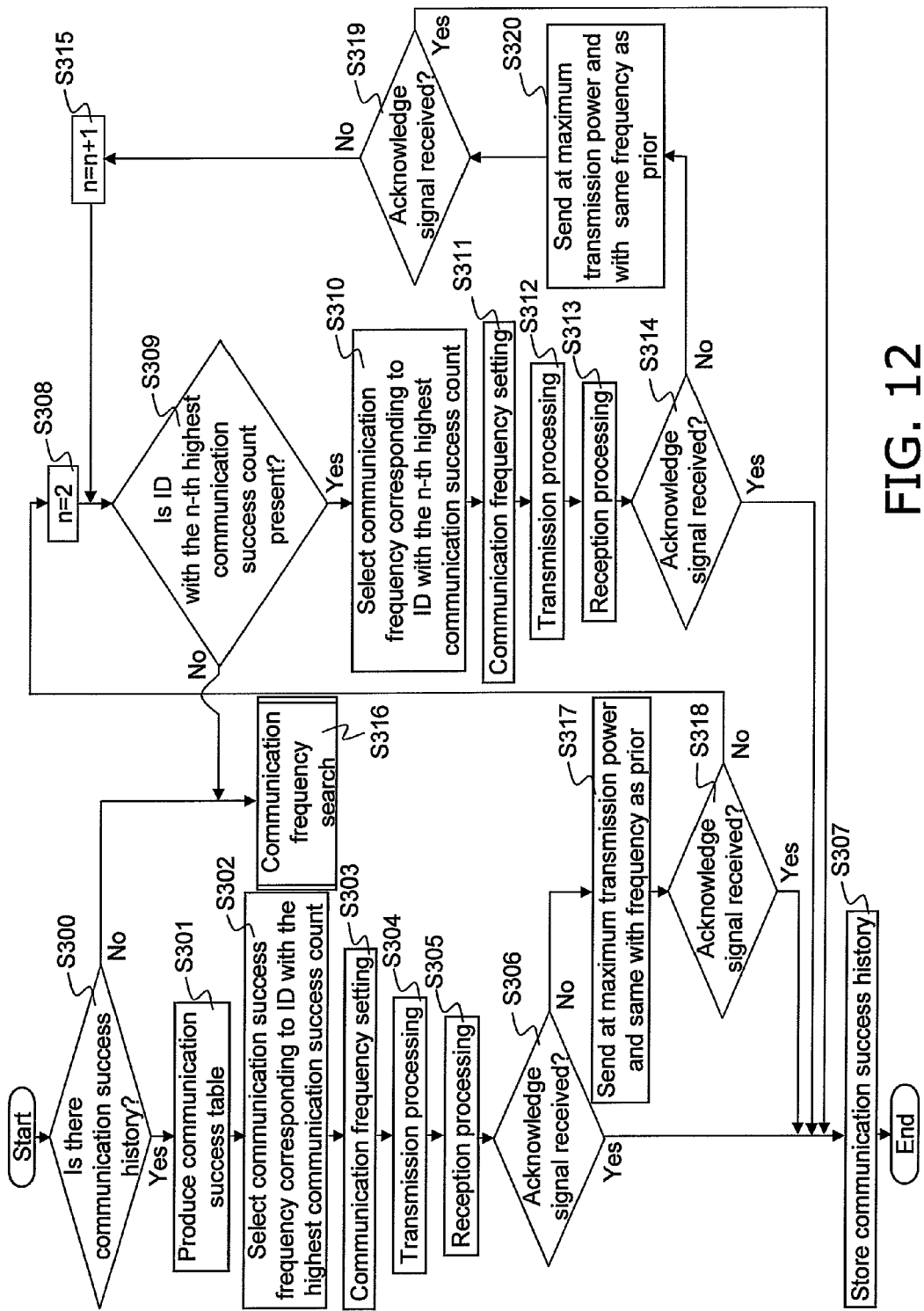
FIG. 12 is a communication frequency selection flowchart with the blood glucose level measurement apparatus in FIG. 11.

Next, the method for selecting the communication frequency performed by the communication frequency selector 61 in this embodiment will be described through reference to FIGS. 12 and 13. FIG. 12 is a flowchart of the communication frequency selection performed by the communication frequency selector 61, and FIG. 13 is a diagram illustrating an example of a communication success table, which gives the communication success count for each portable terminal ID produced from the communication success history stored in the storage component 18.

First, in FIG. 12, when communication begins, in step S300, just as in step S100 shown in FIG. 5, the communication frequency selector 19 checks whether or not a communication success history is present in the storage component 18. If at least one communication success history is present, the flow proceeds to step S301, but if not a single communication success history is present, the flow proceeds to step S316.

Then, in step S301, which is executed if at least one communication success history is present, a communication success table is produced from the communication success history stored in the storage component 18. As shown in FIG. 13, for example, the communication success table here is a compilation of the communication success history of FIG. 6 along with the communication success count for every portable terminal ID. In FIG. 6, portable terminals ID1, ID2, and ID3 are present, so the compilation of the communication success history in FIG. 6 for every portable terminal ID results in what is shown in FIG. 13, and since DATA from DATA0 to DATA15 is present in FIG. 6, the total communication success count of the various portable terminal ID's is 16 in FIG. 13. Of the communication success frequency in FIG. 13, only the most recent communication success frequency for each portable terminal ID is stored. For example, since the most recent communication success frequency for the portable terminal ID1 in FIG. 6 is the 2.42 GHz of DATA1, 2.42 GHz is stored for the communication frequency of ID1 in FIG. 13. The time series order of the portable terminal ID's that appear when the communication success history is viewed going backward in time is also stored. This is because if there are communication success counts of the same value, the communication frequency for the portable terminal ID that is newer in time series order is preferentially selected. In FIG. 6, the portable terminal ID2 is newest, and then ID1, and finally ID3, so as shown in FIG. 13, the time series order is stored in the order of ID2, ID1, and ID3.

In step S302, the communication frequency is selected for the portable terminal with the highest communication success count from the communication success table produced in step S301. For example, in the case of FIG. 13, since ID2 has the highest communication success count (8 times), 2.44 GHz, which is the most recent communication frequency out of the communication frequencies stored in association with ID2, is selected as the communication frequency.

Next, transmission and reception processing are performed in the same manner in step S303 as in step S102 shown in FIG. 5, step S304 as in step S103 shown in FIG. 5, and step S305 as in step S104 shown in FIG. 5.

In step S306, just as in step S105 shown in FIG. 5, if an acknowledge signal has been received from the portable terminal 23, it is determined that communication is successful and the flow proceeds to step S307, but if not acknowledge signal has been received from the portable terminal 23, it is determined that communication failed and the flow moves to step S317. In step S317, the transmission processing 33 is performed at the maximum transmission power and with the same communication frequency left the same. This is performed in order to check whether the cause of the communication failure in the transmission processing 33 of step S304 occurs not by a deviation in the communication frequency, but by the effect of humans or the emission state of interfering radio waves in the surrounding environment and so forth.

In step S318, it is determined whether or not communication is successful at the maximum transmission power setting and at the communication frequency in step S317. The determination in step S318 is made by the same method as in step S105 above. If communication is deemed successful, the flow proceeds to step S307, but if communication is deemed a failure, the flow proceeds to step S308.

Step S307 is the same as step S106 shown in FIG. 5, in which the portable terminal ID and the communication frequency included in the received reply data 34 are written as communication success history to the storage component 18, and the communication success history is updated.

Meanwhile, step S308 is the same as step S107 shown in FIG. 5, in which the value of the communication frequency selection count n is set to 2.

In step S309, it is confirmed from the communication success table whether or not a portable terminal ID with the n-th highest communication success count is present. In FIG. 13, since there are three types of portable terminal ID in the communication success table, if n=4, it is determined that the communication success table contains no communication frequency at which communication is possible, and the flow moves to the communication frequency search step (S316). The communication frequency search step (S316) is the same as step S115 shown in FIG. 5.

If n is less than 4, the flow proceeds to step S310, and in step S310 the communication frequency of the portable terminal ID with the n-th highest communication success count is selected from the communication success table. For example, if n=2 in FIG. 13, the portable terminal ID with the second highest communication success count is ID1, which has a communication success count of 6 times, so a communication frequency of 2.42 GHz, which is the most recent of the communication frequencies stored in association with ID1, is selected as the communication frequency.

Next, the setting of the selected communication frequency is performed just as in step S110 shown in FIG. 5 (step S311), the transmission processing 33 is performed at the set communication frequency just as in step S111 shown in FIG. 5 (step S312), the reception processing 36 is performed with respect to the transmission processing 33 just as in step S112 shown in FIG. 5 (step S313), and it is determined whether or not the transmission processing 33 is successful just as in step S113 shown in FIG. 5 (step S314).

In step S320, the transmission processing 33 is performed at the maximum transmission power and with the communication frequency left the same. This is performed in order to check whether the cause of the communication failure in the transmission processing 33 of step S312 occurs not by a deviation in the communication frequency, but by the effect of humans or the emission state of interfering radio waves in the surrounding environment and so forth.

In step S319, it is determined whether or not communication is successful at the maximum transmission power setting and at the communication frequency in step S320. The determination in step S319 is made by the same method as in step S105 discussed above. If communication is deemed successful, the flow moves on to step S307, but if it is deemed unsuccessful, the flow moves on to step S315.

If the conclusion is that no acknowledge signal could be received, 1 is added to the value of the communication frequency selection count n (step S315), and the processing from step S309 to step S314 is repeated. On the other hand, if an acknowledge signal is received, the flow moves to step S307 and the communication success history is stored.

As discussed above, in this embodiment, first a communication success table is produced by finding a communication success count for every portable terminal ID from the communication success history stored in the storage component 18. The communication frequency closest to the present is selected in time series order, starting with the portable terminal ID with the highest communication success count, on the basis of the communication success table thus produced. If communication is impossible even at the selected communication frequency, a new communication frequency is searched for.

Doing this not only allows communication to be properly established, but also increases the probability that communication will be established before the flow moves to the communication frequency search (step S316), so a communication frequency at which communication is possible can be set in fewer steps. Therefore, the average time it takes to establish communication can be shortened.

Embodiment 3

Figure 14:
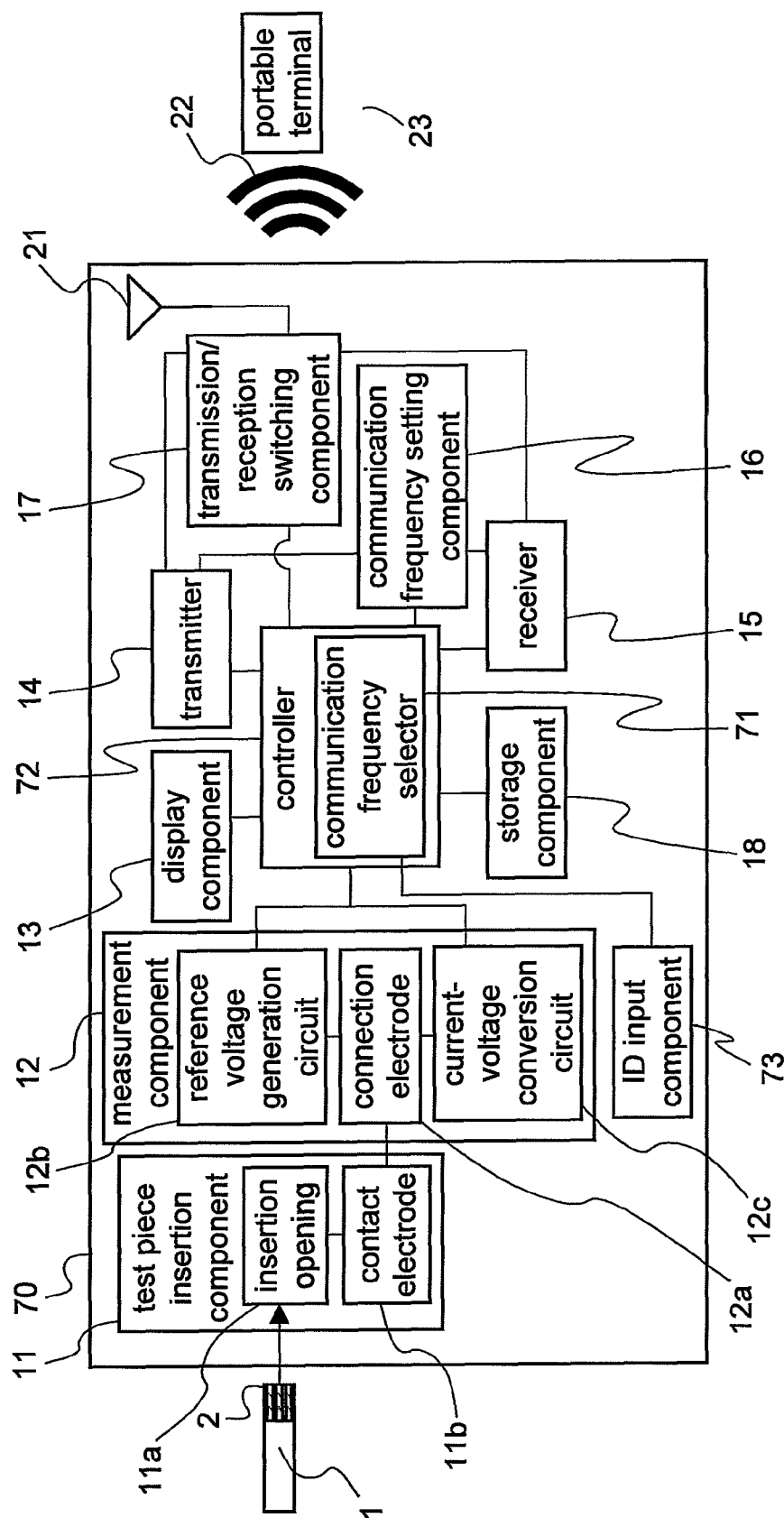
FIG. 14 is a block diagram of the configuration of the blood glucose level measurement apparatus pertaining to a third embodiment.

Next, the configuration of a biological sample measurement apparatus in another embodiment of the present invention will be described through reference to FIG. 14. FIG. 14 is a block diagram of the configuration of a blood glucose level measurement apparatus in this embodiment.

In FIG. 14, a blood glucose level measurement apparatus 70 comprises a test piece insertion component 11 into which the test piece 1 is inserted, a measurement component 12 for measuring the blood glucose level of the user, a display component 13 that allows the user to confirm the measured blood glucose level information, a transmitter 14 for wirelessly transmitting the measured blood glucose level information to a portable terminal 23, a receiver 15 for wirelessly receiving a portable terminal ID sent from the portable terminal 23 and used to identify the portable terminal and an acknowledge signal indicating that communication is successful, a communication frequency setting component 16 for setting the communication frequency at which communication is performed, a transmission/reception switching component 17 for switching between transmission and reception, a storage component 18 that stores various information, a controller 72 that controls the various functions and includes a communication frequency selector 71 for selecting a communication frequency at which communication is possible, an ID input component (individual identification number input component) 73 with which the user can input and specify the desired portable terminal ID, and an antenna 21 that emits a radio wave 22 to the portable terminal 23.

The test piece insertion component 11 includes an insertion opening 11a and a contact electrode 11b, and the measurement component 12 includes a connection electrode 12a, a reference voltage generation circuit 12b, and a current-voltage conversion circuit 12c.

In FIG. 14, components that have the same configuration as described in Embodiment 1 and shown in FIG. 3 are numbered the same and will not be described again. The difference from the blood glucose level measurement apparatus 10 in the first embodiment shown in FIG. 3 is that the ID input component 73 is newly added, and the portable terminal ID of the communication frequency selected by the communication frequency selector 71 can be specified with the ID input component 73. In other words, the communication frequency selector 71 selects the communication frequency closest to the present in time series order is selected from among the communication frequencies stored in association with the portable terminal ID specified by the ID input component 73 in the storage component 18.

Communication Frequency Selection Method of Blood Glucose Level Measurement Apparatus 70

Next, the method for selecting the communication frequency with the blood glucose level measurement apparatus 70 in this embodiment will be described through reference to FIG. 15. FIG. 15 is a flowchart of the communication frequency selection performed in this embodiment.

First, in step S400 in FIG. 15, the portable terminal ID of the portable terminal with which communication is desired is inputted through the ID input component 73. The inputted portable terminal ID is sent to the communication frequency selector 71.

Then, in step S401, it is confirmed whether or not a past communication success history for the inputted portable terminal ID is present in the storage component 18. If a communication success history is present, the flow proceeds to step S402, but if not a single communication success history is present, the flow proceeds to step S408.

Next, in step S402, which is executed if a communication success history is present, the communication frequency closest to the present in time series order is selected from among the communication frequencies stored in association with the inputted portable terminal ID. The communication success history stored in storage component 18 is the same as that in the first embodiment, and for example, as in FIG. 6, the communication frequency and the portable terminal ID are stored in time series order.

Next, transmission and reception processing are performed in the same manner in step S403 as in step S102 shown in FIG. 5, step S404 as in step S103 shown in FIG. 5, and step S405 as in step S104 shown in FIG. 5.

In step S406, just as in step S105 shown in FIG. 5, if an acknowledge signal has been received from the portable terminal 23, it is determined that communication is successful and the flow proceeds to step S407, but if not acknowledge signal has been received from the portable terminal 23, it is determined that communication failed and the flow moves to step S409.

In step S409, the transmission processing 33 is performed at the maximum transmission power and with the communication frequency left the same. This is performed in order to check whether the cause of the communication failure in the transmission processing 33 of step S404 occurs not by a deviation in the communication frequency, but by the effect of humans or the emission state of interfering radio waves in the surrounding environment and so forth.

In step S410, it is determined whether or not communication is successful at the maximum transmission power setting and at the communication frequency in step S409. The determination in step S410 is made by the same method as in step S105 above. If communication is deemed successful, the flow proceeds to step S407, but if communication is deemed a failure, the flow proceeds to step S408.

Step S407 is the same as step S106 shown in FIG. 5, in which the portable terminal ID and the communication frequency included in the received reply data 34 are written as communication success history to the storage component 18, and the communication success history is updated.

Meanwhile, step S408 is the same as step S115 shown in FIG. 5, in which a search is made for a communication frequency at which communication is possible.

As discussed above, in this embodiment, the communication frequency closest to the present in time series order is selected from among the communication frequencies stored in association with the portable terminal ID specified by the ID input component 72, from the communication success history stored in the storage component 18, and communication is performed using the selected communication frequency, and if communication is still impossible, a newer communication frequency is searched for, which allows a communication frequency at which communication is possible to be set in fewer steps.

Also, in this embodiment, since the selected communication frequency is associated with the portable terminal ID specified by the user, if, for example, a single blood glucose level measurement apparatus is used for communication with one portable terminal out of a plurality of specific portable terminals, and the user wishes to begin communication with a specific portable terminal out of these plurality of portable terminals, then it will be possible to preferentially select a communication success history with this specific portable terminal, which is particularly effective.

The present invention is not limited to the above embodiments, and various applications are possible without departing from the gist of the invention. Other embodiments are given below.

Other Embodiments (A)

With the blood glucose level measurement apparatus 10 in the above embodiment, an example is given in which n=n+1 in step S114 shown in FIG. 5, but the present invention is not limited to this.

For example, it may be set so that n=n+2. Here again, of course, since the selected communication frequency is stored in association with the same portable terminal ID, the same effect as above can be obtained, which is that communication can be established more efficiently.

(B)

With the blood glucose level measurement apparatus 10 in the above embodiment, an example is given in which the same portable terminal ID is used in steps S107 to S114 shown in FIG. 5, but the present invention is not limited to this.

For example, the selection may be made going backward in time series order, regardless of the portable terminal ID.

(C)

With the blood glucose level measurement apparatus 60 in the above embodiment, an example is given corresponding to the portable terminal ID with the highest communication success count in step S302 shown in FIG. 12, but the present invention is not limited to this.

For example, any one of the most recent communication frequencies may be selected from among the communication frequencies stored in association with the various portable terminal ID's.

(D)

With the blood glucose level measurement apparatus 60 in the above embodiment, an example is given in which only the most recent communication frequency is selected for each portable terminal ID in steps S301 to S315 shown in FIG. 12, but the present invention is not limited to this.

For example, the constitution may be such that all of the communication frequencies stored in association with the portable terminal ID with the n-th highest communication success count are selected in time series order, after which all of the communication frequencies stored in association with the n+1-th portable terminal ID are selected in time series order.

(E)

With the blood glucose level measurement apparatus 60 in the above embodiment, an example is given in which the flow moved to communication frequency search (S316) when communication is not successful even though all of the most recent communication frequencies are selected for each portable terminal ID in steps S308 to S315 shown in FIG. 12, but the present invention is not limited to this.

For example, the maximum value of n may be set to n=5, so that the flow will move on to communication frequency search even another portable terminal ID has not be selected at this stage.

(F)

With the blood glucose level measurement apparatus 70 in the above embodiment, an example is given in which only the most recent communication frequency stored in association with the portable terminal ID inputted to the ID input component is selected in steps S400 to S408 shown in FIG. 15, but the present invention is not limited to this.

For example, after the most recent communication frequency stored in association with the inputted portable terminal ID has been selected, a communication frequency stored in association with that portable terminal ID may be selected by going backward in time series order. Alternatively, the most recent communication frequency may be selected at first in time series order, after which the flow may move on to step S401.

In the above embodiments, examples are given in which the blood glucose level measurement apparatus 10, 60, or 70 is applied as an example of a biological sample measurement apparatus, but the present invention is not limited to this. For example, it may be a lactic acid measurement apparatus or uric acid measurement apparatus that measures lactic acid, uric acid, or the like, and as long as it is an apparatus that wirelessly transmits this data to another terminal or the like, the effect will be the same as with the blood glucose level measurement apparatus 10, 60, or 70 pertaining to the above embodiments.

INDUSTRIAL APPLICABILITY

With the biological sample measurement apparatus with a wireless communication function pertaining to the present invention, since an individual identification number for the device being communicated with is stored in association with the communication frequency, communication can be established more efficiently, and because of this effect, this apparatus can be widely applied to communication systems and so forth that communicate with apparatus having an individual identification number and can be individually identified.

The invention claimed is:

1. A biological sample measurement apparatus for having wireless communication with a portable terminal, the apparatus comprising:
a biological data measurement component configured to measure biological data;
a transmitter configured to establish communication with the portable terminal using a specific communication frequency, and send the biological data measured by the biological data measurement component to the portable terminal;
a receiver configured to receive a portable terminal individual identification number and a communication success signal sent back from the portable terminal, the communication success signal indicating that communication has been established with the portable terminal using the specific communication frequency;

a storage component configured to store as communication success history the specific communication frequency and the portable terminal individual identification number so as to be associated with the specific communication frequency when the receiver has received the communication success signal; and a communication frequency selector configured to select the specific communication frequency and the portable terminal individual identification number associated with the specific communication frequency before the transmitter starts communication with the portable terminal.

2. The biological sample measurement apparatus according to claim 1, wherein the communication frequency selector selects, for the specific communication frequency, a communication frequency from among the communication success history in time series order, going backward from the most recent communication frequency.

3. The biological sample measurement apparatus according to claim 1, wherein the communication frequency selector selects, for the specific communication frequency, a first communication frequency and a first terminal individual identification number associated with the selected first communication frequency; and when the transmitter fails to establish communication with a portable terminal using the selected first communication frequency, the communication frequency selector further selects, for the specific communication frequency, a second communication frequency that has been stored in the storage component and is associated with the first terminal individual identification number.

4. The biological sample measurement apparatus according to claim 1, wherein the communication frequency selector selects, for the specific communication frequency, a communication frequency from among the most recent communication frequencies for the communication frequencies stored in association with each portable terminal individual identification number.

5. The biological sample measurement apparatus according to claim 1, wherein the communication frequency selector selects, for the specific communication frequency, a communication frequency in descending order of the storage count for each portable terminal individual identification number in the communication success history.

6. The biological sample measurement apparatus according to claim 1, wherein, in the communication success history, when the storage count is the same in number for different portable terminal individual identification numbers, the communication frequency selector selects, for the specific communication frequency, a communication frequency from among the communication frequencies stored in association with the portable terminal individual identification number that is the same in number as the storage count, in time series order starting with the newest.

7. The biological sample measurement apparatus according to claim 1, further comprising an individual identification number input component with which a desired portable terminal individual identification number can be inputted.

8. The biological sample measurement apparatus according to claim 1, wherein the communication frequency selector repeatedly selects, for the specific communication frequency, a communication frequency, focusing on a specific reference frequency and in increasing order of deviation from the specific reference frequency, until the receiver receives the communication success signal or until the deviation reaches or exceeds a specific value.

9. The biological sample measurement apparatus according to claim 8, wherein the deviation is a value obtained by adding or subtracting by a specific frequency value at a time.

10. The biological sample measurement apparatus according to claim 8, wherein the communication frequency selector selects, for the specific communication frequency, a communication frequency in increasing order of deviation from a communication frequency selected when the receiver has received the communication success signal, and searches for a receivable frequency band that is a range of communication frequencies over which the receiver can receive the communication success signal.

11. The biological sample measurement apparatus according to claim 10, wherein the storage component stores as the optimal frequency a central frequency of the receivable frequency band.

12. The biological sample measurement apparatus according to claim 1, wherein when the receiver has failed to properly receive the communication success signal even though the transmitter has sent the biological data to a portable terminal at the specific communication frequency selected by the communication frequency selector, the transmitter resends the biological data to the portable terminal with the transmission power set to maximum at the selected specific communication frequency.

13. The biological sample measurement apparatus according to claim 1, wherein the biological data measurement component includes a reagent layer connected to a working electrode and a counter electrode, the reagent layer being configured to react with a biological specimen to measure the biological data.

* * * * *